US008912152B2

(12) United States Patent
Bovolenta

(10) Patent No.: US 8,912,152 B2
(45) Date of Patent: Dec. 16, 2014

(54) HIV VIF MUTANTS

(75) Inventor: Chiara Bovolenta, Milan (IT)

(73) Assignee: MolMed Spa, Milan (IT)

( * ) Notice: Subject to any disclaimer, the term of this patent is extended or adjusted under 35 U.S.C. 154(b) by 1383 days.

(21) Appl. No.: 11/815,490

(22) PCT Filed: Mar. 7, 2006

(86) PCT No.: PCT/IB2006/001519
§ 371 (c)(1),
(2), (4) Date: Jan. 9, 2008

(87) PCT Pub. No.: WO2006/111866
PCT Pub. Date: Oct. 26, 2006

(65) Prior Publication Data

US 2008/0286248 A1 Nov. 20, 2008

(30) Foreign Application Priority Data

Mar. 8, 2005 (GB) .................................. 0504770.9
May 26, 2005 (GB) .................................. 0510888.1

(51) Int. Cl.
*A61K 48/00* (2006.01)
*C07K 14/005* (2006.01)
*A61K 38/00* (2006.01)

(52) U.S. Cl.
CPC ..... *C07K 14/005* (2013.01); *C12N 2740/16322* (2013.01); *A61K 38/00* (2013.01); *C12N 2740/15043* (2013.01)
USPC ....... 514/44 R; 530/350; 514/1.1; 435/320.1; 536/23.72

(58) Field of Classification Search
None
See application file for complete search history.

(56) References Cited

U.S. PATENT DOCUMENTS

2004/0086488 A1* 5/2004 Kingsman et al. ........... 424/93.2
2004/0234956 A1* 11/2004 Kabat et al. ....................... 435/5

OTHER PUBLICATIONS

Reddy et al., Comparative analyses of human immunodeficiency virus type 1 (HIV-1) and HIV-2 Vif mutants, J Virol. 69(6):3549-53, 1995.*

Lauer et al., A prototype transduction tag system (delta LNGFR/NGF) for noninvasive clinical gene therapy monitoring, Cancer Gene Ther. 7(3):430-7, 2000.*

Lauer et al. "A prototype transduction tag system (delta LNGFR/NGF) for noninvasive clinical gene therapy monitoring." Cancer Gene Ther.( 2000); 7(3): pp. 430-437.*

UK Search Report dated Nov. 14, 2005, priority application GB0510888.1.

Yedavilla et al., UNIPROT Acc. No. 057309_HIV1 Seq. D142CC4DB8BA3E33 & J Virology 72: 1092-1102, 1998.

Addo et al., Comprehensive epitope analysis of human immunodeficiency virus type 1 (HIV-1)-specific T-cell responses directed against the entire expressed HIV-1 genome demonstrate broadly directed responses, but no correlation to viral load, J. Virol., 77:2081-2092, 2003.

Adekale et al., Changes in the Vif protein of HIF-1 associated with the development of resistance to inhibitors of viral protease, J. Med. Virol., 75:195-201, 2005.

Aldrovandi et al., Replication and pathogenicity of human immunodeficiency virus type 1 accessory gene mutants in SCID-hu mice, J. Virol., 70:1505-1511, 1996.

Baraz et al., The Vif protein of human immunodeficiency virus type 1 (HIV-1): enigmas and solutions, Curr. Med. Chem., 11:221-231, 2004.

Baum et al., Side effects of retroviral gene transfer into hematopoeitic stem cells, Blood, 101:2099-2114, 2003.

Blankson et al., The challenge of viral reservoirs in HIV-1 infection, Annu. Rev. Med., 53:557-593, 2002.

Bonini et al., HSV-TK gene transfer into donor lymphocytes for control of allogeneic graft-versus-leukemia, Science, 276:1719-1724, 1997.

Bonini et al., Safety of retroviral gene marking with a truncated NGF receptor, Nat. Med., 9:367-369, 2003.

Borman et al., Human immunodeficiency virus type 1 Vif mutant particles from restrictive cells: role of Vif in correct particle assembly and infectivity, J. Virol., 69:2058-2067, 1995.

Bouyac et al., Phenotypically Vif human immunodeficiency virus type 1 is produced by chronically infected restrictive cells, J. Virol., 71:2473-2477, 1997.

Bovolenta et al., Human T-Cell leukemia virus type 2 induces survival and proliferation of $CD34^+$ TF-1 cells through activation of STAT1 and STAT5 by secretion of interferon-γ and granulocyte macrophage-colony-stimulating factor, Blood, 99:224-231, 2002.

Buchschacher et al., Approaches to gene therapy for human immunodeficiency virus infection, Hum. Gene Ther., 12:1013-1019, 2001.

Carlini et al., Analysis of a non producer HIV-1 proviral clone (F12) by construction of molecular chimeras with an infectious molecular clone, Int. Conf. AIDS, Abstract PuA6141, Jul. 19-24, 1992.

Carlini et al., The non-producer phenotype of the human immunodeficiency virus type 1 provirus F12/HIV-1 is the result of multiple genetic variations, J. Gen. Virol., 77:2009-2013, 1996.

Clouse et al., Monokine regulation of human immunodeficiency virus-1 expression in a chronically infected human T cell clone, J. Immunol., 142:431-438, 1989.

Coburn et al., Potent and specific inhibition of human immunodeficiency virus type 1 replication by RNA interference, J. Virol., 76:9225-9231, 2002.

(Continued)

*Primary Examiner* — Thaian N Ton
*Assistant Examiner* — Titilayo Moloye
(74) *Attorney, Agent, or Firm* — Marshall, Gerstein & Borun LLP

(57) ABSTRACT

A polynucleotide comprising a nucleotide sequence encoding Vif, wherein each of the amino acids corresponding to positions 127, 128, 130, 131, 132 and 142 of the amino acid sequence in FIG. 1A representing the Vif wild-type consensus sequence, are replaced with another amino acid, and wherein the nucleotide sequence does not encode the amino acid sequence shown in FIG. 2, representing the Vif sequence of the F12 non-producer variant of HIV-1.

13 Claims, 19 Drawing Sheets

(56) References Cited

OTHER PUBLICATIONS

Cullen et al., HIV-1 auxiliary proteins: making connections in a dying cell, Cell, 93:685-692, 1998.
D'Aloja et al., *gag, vif*, and *nef* genes contribute to the homologous viral interference induced by a nonproducer human immunodeficiency virus type 1 (HIV-1) variant : identification of novel HIV-1-inhibiting viral protein mutants, J. Virol., 72:4308-4019, 1998.
Desrosiers et al., Identification of highly attenuated mutants of simian immunodeficiency virus, J. Virol., 72:1431-1437, 1998.
Dettenhofer et al., Association of human immunodeficiency virus type 1 Vif with RNA and its role in reverse transcription, J. Virol. ,74:8938-8945, 2000.
Dull et al., A third-generation lentivirus vector with a conditional packaging system, J. Virol, 72:8463-8471, 1998.
Emerman et al., The *rev* gene product of the human immunodeficiency virus affects envelope-specific RNA localization, Cell, 57:1155-1165, 1989.
Federico et al., Biologic and molecular characterization of producer and nonproducer clones from HUT-78 cells infected with a patient HIV isolate, AIDS Res. Hum. Retroviruses, 5:385-396, 1989.
Ferrari et-al., An in vivo model of somatic cell gene therapy for human severe combined immunodeficiency, Science, 251:1363-1366, 1991.
Fisher et al., The sor gene of HIV-1 is required for efficient virus transmission in vitro, Science, 237:888-893, 1987.
Folks et al., Characterization of a continuous T-cell line susceptible to the cytopathic effects of the acquired immunodeficiency syndrome (AIDS)-associated retrovirus, PNAS USA, 82:4539-4543, 1985.
Folks et al., Cytokine-induced expression of HIV-1 in a chronically infected promonocyte cell line, Science, 238:800-802, 1987.
Folks et al., Tumor necrosis factor $\alpha$ induces expression of human immunodeficiency virus in a chronically infected T-cell clone, PNAS USA, 86:2365-2368, 1989.
Follenzi et al., Gene transfer by lentiviral vectors is limited by nuclear translocation and rescued by HIV-1 *pol* sequences, Nat. Genet., 25:217-222, 2000.
Fouchier et al., Human immunodeficiency virus type 1 Vif does not influence expression or virion incorporation of *gag-*, *pol-*, and *env*-encoded proteins, J. Virol., 70:8263-8269, 1996.
Frankel et al., HIV-1: fifteen proteins and an RNA, Annu. Rev. Biochem., 67:1-25, 1998.
Fujita et al., Expression of HIV-1 accessory protein Vif is controlled uniquely to be low and optimal by proteasome degradation, Microbes Infect., 6:791-798, 2004.
Gabuzda et al., Role of *vif* in replication of human immunodeficiency virus type 1 in $CD4^+$ T lymphocytes, J. Virol., 66:6489-6495,1992.
GenBank accession No. AF033811, Moloney murine leukemia virus, complete genome, Dec. 3, 1998.
GenBank accession No. AF033819, HIV-1, complete genome, Aug. 28, 2002.
GenBank accession No. K02007, Human immunodeficiency virus type 1, isolate ARV-2/SF2, complete proviral genome, Aug. 11, 1995.
GenBank accession No. K02013 (BRU), Human immunodeficiency virus type 1, isolate BRU, complete genome (LAV-1), Aug. 2, 1993.
GenBank accession No. K02083, Human immunodeficiency virus type 1, isolate PV22, complete genome (H9/HTLV-III proviral DNA), Oct. 1, 1999.
GenBank accession No. K03455, Human immunodeficiency virus type 1 (HXB2), complete genome; HIV1/HTLV-III/LAV reference genome, Oct. 21, 2002.
GenBank accession No. M17449, Human immunodeficiency virus type 1, isolate MN, complete genome, Aug. 2, 1993.
GenBank accession No. M19921, Human immunodeficiency virus type 1, NY5/BRU (LAV-1) recombinant clone pNL4-3, Aug. 2, 1993.
GenBank accession No. Z11530, Human immunodeficiency virus I (HIV-1) RNA, Nov. 14, 2006.
Gibbs et al., Construction and in vitro properties of HIV-1 mutants with deletions in "nonessential" genes, AIDS Res. Hum. Retroviruses, 10:343-350, 1994.
Goncalves et al., Subcellular localization of the Vif protein of human immunodeficiency virus type 1, J. Virol., 68:704-712, 1994.
Grignani et al., High-efficiency gene transfer and selection of human hematopoietic progenitor cells with a hybrid EBV/retroviral vector expressing the green fluorescence protein, Cancer Res., 58, 14-19, 1998.
Harris et al., DNA deamination mediates innate immunity to retroviral infection, Cell, 113:803-809, 2003.
Ho et al., The HIV-1 vaccine race, Cell, 110:135-138, 2002.
Höglund et al., Role of Vif during packing of the core of HIV-1, Virology, 201:349-355, 1994.
International Search Report, PCT/IB2006/001519, European Patent Office, Jan. 18, 2007.
Jacque et al., Modulation of HIV-1 replication by RNA interference, Nature, 418:435-438, 2002.
Kao et al., The Human immunodeficiency virus type 1 Vif protein reduces intracellular expression and inhibits packaging of APOBEC3G (CEM15), a cellular inhibitor of virus infectivity, J. Virol., 77:11398-11407, 2003.
Lecossier et al., Hypermutation of HIV-1 DNA in the absence of the Vif protein, Science, 300:1112, 2003.
Lee et al., Expression of small interfering RNAs targeted against HIV-1 *rev* transcripts in human cells, Nat. Biotechnol., 20:500-505, 2002.
Liu et al., The Vif protein of human and simian immunodeficiency viruses is packaged into virions and associates with viral core structures, J. Virol., 69:7630-7638, 1995.
Lusso et al., Growth of macrophage-topic and primary human immunodeficiency virus type 1 (HIV-1) isolates in a unique $CD4^+$ T-cell clone (PM1): failure to downregulate CD4 and to interfere with cell-line-tropic HIV-1, J. Virol., 69:3712-3720, 1995.
Malim et al., The HIV-1 *rev* trans-activator acts through a structured target sequence to activate nuclear export of unspliced viral mRNA, Nature, 338:254-257, 1989.
Mariani et al., Species-specific exclusion of APOBEC3G from HIV-1 virions by Vif, Cell, 114:21-31, 2003.
Mavilio et al., Peripheral blood lymphocytes as target cells of retroviral vector-mediated gene transfer, Blood, 83:1988-1997, 1994.
Nara et al., Quantitative infectivity assay for HIV-1 and-2, Nature, 332:469-470, 1988.
Navarro et al., Recent insights into HIV-1 Vif, Curr. Opin. Immunol., 16:477-482, 2004.
Novina et al., siRNA-directed inhibition of HIV-1 infection, Nat. Med., 8:681-686, 2002.
Qin et al., Inhibiting HIV-1 infection in human T cells by lentiviral-mediated delivery of small interfering RBA against CCR5, PNAS USA, 100:183-188, 2003.
Ranga et al., Enhanced T Cell engraftment after retroviral delivery of an antiviral gene in HIV-infected individuals, PNAS USA, 95:1201-1206, 1998.
Re et al., HIV-1 Vpr: G2 cell cycle arrest, macrophages and nuclear transport, Prog. Cell Cycle Res., 3:21-27, 1997.
Richman, HIV chemotherapy, Nature, 410:995-1001, 2001.
Sheehy et al., Isolation of a human gene that inhibits HIV-1 infection and is suppressed by the viral VIF protein, Nature, 418:646-650, 2002.
Simon et al., Mutational analysis of the human immunodeficiency virus type 1 Vif protein, J. Virol., 73:2675-2681, 1999.
Simon et al., The human immunodeficiency virus type 1 Vif protein modulates the postpenetration stability of viral nucleoprotein complexes. J. Virol., 70:5297-5305, 1996.
Smith et al., Monoclonal antibody and enzymatic profiles of human malignant T-lymphoid cells and derived cell lines, Cancer Res., 44:4657-4660, 1984.
Soneoka et al., A transient three-plasmid expression system for the production of high titer retroviral vectors, Nucl. Acids Res., 23:628-633,1995.
Sova et al., Conservation of an intact human immunodeficiency virus type 1 *vif* gene in vitro and in vivo, J. Virol., 69:2557-2564, 1995.
Sova et al., Vif is largely absent from human immunodeficiency virus type 1 mature virions and associates mainly with viral particles containing unprocessed *gag*, J. Virol., 75:5504-5517, 2001.

(56) References Cited

OTHER PUBLICATIONS

Subbramanian et al., Human immunodeficiency virus type 1 Vpr is a positive regulator of viral transcription and infectivity in primary human macrophages, J. Exp. Med., 187:1103-1111, 1998.

Taddeo et al., Homologous superinfection of both producer and nonproducer HIV-infected cells is blocked at a late retrotranscription step, Virology, 194:441-452, 1993.

Taddeo et al., Reversion of a human immunodeficiency virus type 1 integrase mutant at a second site restores enzyme function and virus infectivity, J. Virol., 70:8277-8284, 1996.

Teng et al., Molecular cloning of an apolipoprotein B messenger RNA editing protein, Science, 260:1816-1819, 1993.

Trono, Retroviruses under editing crossfire: a second member of the human APOBEC3 family is a Vif-blockable innate antiretroviral factor, EMBO Rep., 5:679-680, 2004.

Vallanti et al., T lymphocytes transduced with a lentiviral vector expressing F12-Vif are protected from HIV-1 infection in an APOBEC3G-independent manner, Mol. Ther., 12:697-706, 2005.

Vicenzi et al., Envelope-dependent restriction of human immunodeficiency virus type 1 spreading in $CD4^+$ T lymphocytes: R5 but not X4 viruses replicate in the absence of T-cell receptor restimulation, J. Virol., 73:7515-7523, 1999.

Vodicka et al., HIV-1 Vpr interacts with the nuclear transport pathway to promote macrophage infection, Genes Dev., 12:175-185, 1998.

Von Schwedler et al., *vif* is crucial for human immunodeficiency virus type 1 proviral DNA synthesis in infected cells, J. Virol., 67:4945-4955, 1993.

Wieland et al., Diversity of the Vif gene of human immunodeficiency virus type 1 in Uganda, J. Gen. Virol., 78:393-400, 1997.

Wieland et al., In vivo genetic variability of the HIV-1 Vif gene, Virology, 203:43-51, 1994.

Woffendin et al., Expression of a protective gene prolongs survival of T cells in human immunodeficiency virus-infected patients, PNAS USA, 93:2889-2894, 1996.

Wong-Staal et al., A controlled, phase 1 clinical trial to evaluate the safety and effects in HIV-1 infected humans of autologous lymphocytes transduced with a ribozyme that cleaves HIV-1 RNA, Hum. Gene Ther., 9:2407-2425, 1998.

Written Opinion of the International Searching Authority, PCT/IB2006/001519, European Patent Office, Jan. 18, 2007.

Yang et al., The multimerization of human immunodeficiency virus type I Vif protein, J. Biol. Chem., 276:4889-4893, 2001.

Zhang et al., Human immunodeficiency virus type 1 Vif protein is an integral component of an mRNP complex of viral RNA and could be involved in the viral RNA folding and packaging process, J. Virol., 74:8252-8261, 2000.

Zimmerman et al., Identification of a host protein essential for assembly of immature HIV-1 capsids, Nature, 415:88-92, 2002.

Zufferey et al., Multiply attenuated lentiviral vector achieves efficient gene delivery in vivo, Nat. Biotechnol., 15:871-875, 1997.

Zufferey et al., Self-inactivating lentivirus vector for safe and efficient in vivo gene delivery, J. Virol., 72:9873-9880, 1998.

* cited by examiner

Figure 1A. WT-Vif Consensus sequence (SEQ ID NO: 1)

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro His
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu His Tyr Phe
            100                 105                 110

Asp Cys Phe Ser Glu Ser Ala Ile Arg Lys Ala Leu Leu Gly His Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
            180                 185                 190
```

Figure 1B. Consensus sequence alignments

| | 5 | 15 | 25 | 35 | 45 | 55 |
|---|---|---|---|---|---|---|
| HXB2 | MENRWQVMIV | WQVDRMRIRT | WKSLVKHHMY | VSGKARGWFY | RHHYESPHPR | ISSEVHIPLG |
| BRU | MENRWQVMIV | WQVDRMRIRT | WKSLVKHHMY | VSGKARGWFY | RHHYESPHPR | ISSEVHIPLG |
| SF2 | MENRWQVMIV | WQVDRMRIRT | WKSLVKHHMY | ISKKAKGWFY | RHHYESTHPR | VSSEVHIPLG |
| PV22 | MENRWQVMIV | WQVDRMRIRT | WKSLVKHHMY | VSGKARGWFY | RHHYESPHPR | ISSEVHIPLG |
| MN | MENRRQVMIV | WQADRMRIRT | WKSLVKHHMY | ISKKAKGRFY | RHHYESTHPR | ISSEVHIPLG |
| F12Vif | MENRWQVMIV | WQVDRMRIRT | WISLVKHHIY | ISKKAKGWFY | KHHYESTNPR | ISSEVHIPLG |
| Consensus | MENRWQVMIV | WQVDRMRIRT | WKSLVKHHMY | VSGKARGWFY | RHHYESPHPR | ISSEVHIPLG |

| | 65 | 75 | 85 | 95 | 105 | 115 |
|---|---|---|---|---|---|---|
| HXB2 | DARLVITTYW | GLHTGERDWH | LGQGVSIEWR | KKRYSTQVDP | ELADQLIHLY | YFDCFSDSAI |
| BRU | DARLVITTYW | GLHTGERDWH | LGQGVSIEWR | KKRYSTQVDP | ELADQLIHLY | YFDCFSDSAI |
| SF2 | DAKLVITTYW | GLHTGEREWH | LGQGVAIEWR | KKKYSTQVDP | GLADQLIHLH | YFDCFSESAI |
| PV22 | DARLVITTYW | GLHTGERDWH | LGQGVSIEWR | KKRYSTQVDP | ELADQLIHLY | YFDCFSDSAI |
| MN | DARLVITTYW | GLHTGERDWH | LGQGVSIEWR | KKRYSTQVDP | DLADHLIHLH | YFDCFSDSAI |
| F12Vif | DARLVVTTYW | GLHTGERDWN | LGQGVSIEWR | KKRYSTQVDP | GLADQLIHRY | YFDCFSESAI |
| Consensus | DARLVITTYW | GLHTGERDWH | LGQGVSIEWR | KKRYSTQVDP | ELADQLIHLY | YFDCFSDSAI |

| | 125 | 135 | 145 | 155 | 165 | 175 |
|---|---|---|---|---|---|---|
| HXB2 | RKALLGHIVS | PRCEYQAGHN | KVGSLQYLAL | AALITPKKIK | PPLPSVTKLT | EDRWNKPQKT |
| BRU | RKALLGHIVS | PRCEYQAGHN | KVGSLQYLAL | AALITPKKIK | PPLPSVTKLT | EDRWNKPQKT |
| SF2 | KNAILGYRVS | PRCEYQAGHN | KVGSLQYLAL | AALITPKKTK | PPLPSVKKLT | EDRWNKPQKT |
| PV22 | RKALLGHIVS | PRCEYQAGHN | KVGSLQYLAL | AALITPKKIK | PPLPSVTKLT | EDRWNKPQKT |
| MN | RKAILGHRVS | PICEFQAGHN | KVGPLQYLAL | TALITPKKIK | PPLPSVKKLT | EDRWNKPQKT |
| F12Vif | RNAILGNVVR | LSCEYQAGHN | KIGSLQYLAL | AALITPKKIK | PPLPSVTKLT | EDRWNKPQKT |
| Consensus | RKALLGHIVS | PRCEYQAGHN | KVGSLQYLAL | AALITPKKIK | PPLPSVTKLT | EDRWNKPQKT |

| | 185 | | |
|---|---|---|---|
| HXB2 | KGHRGSHTMN | GH | (SEQ ID NO: 2) |
| BRU | KGHRGSHTMN | GH | (SEQ ID NO: 3) |
| SF2 | KGHRGSHTMN | GH | (SEQ ID NO: 4) |
| PV22 | KGHRGSHTMN | GH | (SEQ ID NO: 5) |
| MN | KGHRGSHTIN | GH | (SEQ ID NO: 6) |
| F12Vif | KGHRRNHTMN | GH | (SEQ ID NO: 7) |
| Consensus | KGHRGSHTMN | GH | (SEQ ID NO: 1) |

Figure 1C. NL4-3 Vif Sequence

MENRWQVMIVWQVDRMRINTWKRLVKHHMYISRKAKDWFYRHHYESTNPKISSEVHIPLGDAKLVITTYWGLHTGER
DWHLGQGVSIEWRKKRYSTQVDPDLADQLIHLHYFDCFSESAIRNTILGRIVSPRCEYQAGHNKVGSLQYLALAALI
KPKQIKPPLPSVRKLTEDRWNKPQKTKGHRGSHTMNGH (SEQ ID NO: 8)

Figure 2. F12-Vif (SEQ ID NO: 7)

```
Met Glu Asn Arg Trp Gln Val Met Ile Val Trp Gln Val Asp Arg Met
1               5                   10                  15

Arg Ile Arg Thr Trp Ile Ser Leu Val Lys His His Ile Tyr Ile Ser
            20                  25                  30

Lys Lys Ala Lys Gly Trp Phe Tyr Lys His His Tyr Glu Ser Thr Asn
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Gly Leu Ala Asp Gln Leu Ile His Arg Tyr Tyr Phe
            100                 105                 110

Asp Cys Phe Ser Glu Ser Ala Ile Arg Asn Ala Ile Leu Gly Asn Val
        115                 120                 125

Val Arg Leu Ser Cys Glu Tyr Gln Ala Gly His Asn Lys Ile Gly Ser
    130                 135                 140
```

Figure 3A. Chim1 (SEQ ID NO: 9)

```
Met Glu Asn Arg Trp Gln Val Met Ile Val Trp Gln Val Asp Arg Met
1               5                   10                  15

Arg Ile Arg Thr Trp Ile Ser Leu Val Lys His His Ile Tyr Ile Ser
            20                  25                  30

Lys Lys Ala Lys Gly Trp Phe Tyr Lys His His Tyr Glu Ser Thr Asn
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190
```

Figure 3B. Chim1 (SEQ ID NO: 9)

*MENRWQVMIVWQVDRMRIRTWISLVKHHIYISKKAKGWFYKHHYESTNPRISSEVHIPLGDAR*
*LVVTTYWGLHTGERDWNLGQGVSI*EWRKKRYSTQVDPDLADQLIHLHYFDCFSESAIRNTI
LGRIVSPRCEYQAGHNKVGSLQYLALAALIKPKQIKPPLPSVRKLTEDRWNKPQKTKGHR
GSHTMNGH

Figure 4A. Chim2 (SEQ ID NO: 10)

| | | | | | | | | | | | | | | | |
|---|---|---|---|---|---|---|---|---|---|---|---|---|---|---|---|
| Met | Glu | Asn | Arg | Trp | Gln | Val | Met | Ile | Val | Trp | Gln | Val | Asp | Arg | Met |
| 1 | | | | 5 | | | | | 10 | | | | | 15 | |
| Arg | Ile | Asn | Thr | Trp | Lys | Arg | Leu | Val | Lys | His | His | Met | Tyr | Ile | Ser |
| | | | 20 | | | | | 25 | | | | | 30 | | |
| Arg | Lys | Ala | Lys | Asp | Trp | Phe | Tyr | Arg | His | His | Tyr | Glu | Ser | Thr | Asn |
| | | 35 | | | | | 40 | | | | | 45 | | | |
| Pro | Lys | Ile | Ser | Ser | Glu | Val | His | Ile | Pro | Leu | Gly | Asp | Ala | Lys | Leu |
| | 50 | | | | | 55 | | | | | 60 | | | | |
| Val | Ile | Thr | Thr | Tyr | Trp | Gly | Leu | His | Thr | Gly | Glu | Arg | Asp | Trp | His |
| 65 | | | | | 70 | | | | | 75 | | | | | 80 |
| Leu | Gly | Gln | Gly | Val | Ser | Ile | Glu | Trp | Arg | Lys | Lys | Arg | Tyr | Ser | Thr |
| | | | | 85 | | | | | 90 | | | | | 95 | |
| Gln | Val | Asp | Pro | Gly | Leu | Ala | Asp | Gln | Leu | Ile | His | **Arg** | Tyr | Tyr | Phe |
| | | | 100 | | | | | 105 | | | | | 110 | | |
| Asp | Cys | Phe | Ser | Glu | Ser | Ala | Ile | Arg | Asn | Ala | Ile | Leu | Gly | **Asn** | **Val** |
| | | 115 | | | | | 120 | | | | | 125 | | | |
| Val | **Arg** | **Leu** | **Ser** | Cys | Glu | Tyr | Gln | Ala | Gly | His | Asn | Lys | **Ile** | Gly | Ser |
| | 130 | | | | | 135 | | | | | 140 | | | | |
| Leu | Gln | Tyr | Leu | Ala | Leu | Ala | Ala | Leu | Ile | Thr | Pro | Lys | Lys | Ile | Lys |
| 145 | | | | | 150 | | | | | 155 | | | | | 160 |
| Pro | Pro | Leu | Pro | Ser | Val | Thr | Lys | Leu | Thr | Glu | Asp | Arg | Trp | Asn | Lys |
| | | | | 165 | | | | | 170 | | | | | 175 | |
| Pro | Gln | Lys | Thr | Lys | Gly | His | Arg | **Arg** | **Asn** | His | Thr | Met | Asn | Gly | His |
| | | | 180 | | | | | 185 | | | | | 190 | | |

Figure 4B. Chim2 (SEQ ID NO: 10)

MENRWQVMIVWQVDRMRINTWKRLVKHHMYISRKAKDWFYRHHYESTNPKISSEVHIP
LGDAKLVITTYWGLHTGERDWHLGQGVSIE*WRKKRYSTQVDPGLADQLIH**R**YYFDCFSESAI*
*RNAILGN**VVRLSCEYQAGHNKIGSLQYLALAALITPKKIKPPLPSVTKLTEDRWNKPQKTKGHRR*
*N**HTMNGH*

Figure 5A. Chim3 (SEQ ID NO: 11)

| | | | | | | | | | | | | | | | |
|---|---|---|---|---|---|---|---|---|---|---|---|---|---|---|---|
| Met | Glu | Asn | Arg | Trp | Gln | Val | Met | Ile | Val | Trp | Gln | Val | Asp | Arg | Met |
| 1 | | | | 5 | | | | | 10 | | | | | 15 | |
| Arg | Ile | Asn | Thr | Trp | Lys | Arg | Leu | Val | Lys | His | His | Met | Tyr | Ile | Ser |
| | | | 20 | | | | | 25 | | | | | 30 | | |
| Arg | Lys | Ala | Lys | Asp | Trp | Phe | Tyr | Arg | His | His | Tyr | Glu | Ser | Thr | Asn |
| | | 35 | | | | | 40 | | | | | 45 | | | |
| Pro | Lys | Ile | Ser | Ser | Glu | Val | His | Ile | Pro | Leu | Gly | Asp | Ala | Lys | Leu |
| | 50 | | | | | 55 | | | | | 60 | | | | |
| Val | Ile | Thr | Thr | Tyr | Trp | Gly | Leu | His | Thr | Gly | Glu | Arg | Asp | Trp | His |
| 65 | | | | | 70 | | | | | 75 | | | | | 80 |
| Leu | Gly | Gln | Gly | Val | Ser | Ile | Glu | Trp | Arg | Lys | Lys | Arg | Tyr | Ser | Thr |
| | | | | 85 | | | | | 90 | | | | | 95 | |
| Gln | Val | Asp | Pro | Asp | Leu | Ala | Asp | Gln | Leu | Ile | His | Leu | His | Tyr | Phe |
| | | | 100 | | | | | 105 | | | | | 110 | | |
| Asp | Cys | Phe | Ser | Glu | Ser | Ala | Ile | Arg | Asn | Thr | Ile | Leu | Gly | **Asn** | **Val** |
| | | 115 | | | | | 120 | | | | | 125 | | | |
| Val | **Arg** | **Leu** | **Ser** | Cys | Glu | Tyr | Gln | Ala | Gly | His | Asn | Lys | Ile | Gly | Ser |
| | 130 | | | | | 135 | | | | | 140 | | | | |
| Leu | Gln | Tyr | Leu | Ala | Leu | Ala | Ala | Leu | Ile | Thr | Pro | Lys | Lys | **Ile** | Lys |
| 145 | | | | | 150 | | | | | 155 | | | | | 160 |
| Pro | Pro | Leu | Pro | Ser | Val | Thr | Lys | Leu | Thr | Glu | Asp | Arg | Trp | Asn | Lys |
| | | | | 165 | | | | | 170 | | | | | 175 | |
| Pro | Gln | Lys | Thr | Lys | Gly | His | Arg | Gly | Ser | His | Thr | Met | Asn | Gly | His |
| | | | 180 | | | | | 185 | | | | | 190 | | |

Figure 5B. Chim3 (SEQ ID NO: 11)

MENRWQVMIVWQVDRMRINTWKRLVKHHMYISRKAKDWFYRHHYESTNPKISSEVHI
PLGDAKLVITTYWGLHTGERDWHLGQGVSIEWRKKRYSTQVDPDLADQLIHLHYFDCF
SESAIRNTIL*GNVVRLSCEYQAGHNKIGSLQYLALAALITPKKIKPPLPSVTKL*TEDRWNKPQK
TKGHRGSHTMNGH

Figure 6. Schematic representation of the PΔN, WT-VifPΔN, F12-VifPΔN, Chim1PΔN, Chim2PΔN, and Chim3PΔN lentiviral vectors in their proviral forms.
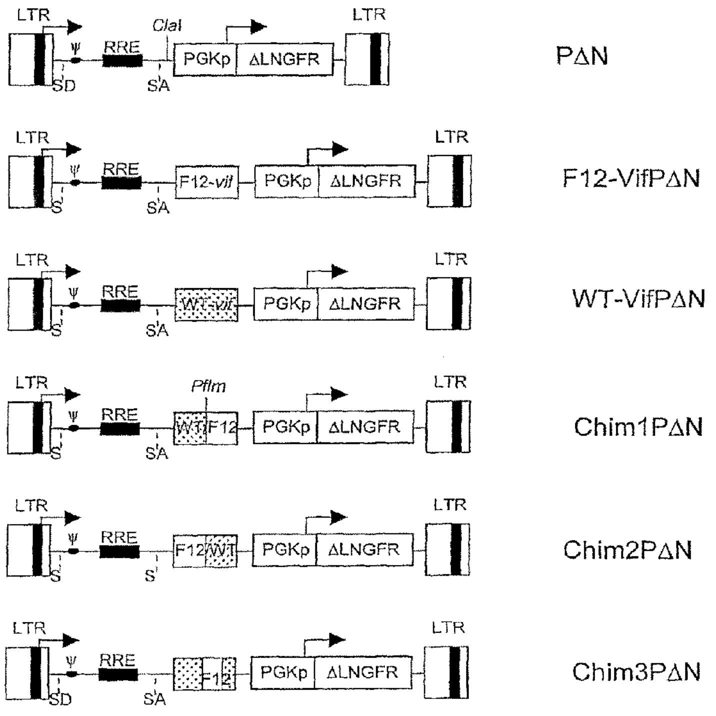

CEM A3.01 NL4-3Δ-*vif* X4 MOI 0,1
Infection #179

CHIM3 (SEQ ID NO: 12)

ATCGATGGGATTATGGAAAACAGATGGCAGGTGATGATTGTGTGGCAAGTAGACAGGA
TGAGGATTAACACATGGAAAAGATTAGTAAAACACCATATGTATATTTCAAGGAAAGC
TAAGGACTGGTTTTATAGACATCACTATGAAAGTACTAATCCAAAAATAAGTTCAGAA
GTACACATCCCACTAGGGGATGCTAAATTAGTAATAACAACATATTGGGGTCTGCATA
CAGGAGAAAGAGACTGGCATTTGGGTCAGGGAGTCTCCATAGAATGGAGGAAAAAGA
GATATAGCACACAAGTAGACCCTGACCTAGCAGACCAACTAATTCATCTGCACTATTTT
GATTGTTTTTCAGAATCTGCTATAAGAAATACCATATTAGGAAATGTAGTTAGACTTAG
TTGTGAATATCAAGCAGGACATAACAAGATAGGATCTCTACAATACTTGGCACTAGCA
GCATTAATAACACCAAAAAAGATAAAGCCACCTTTGCCTAGTGTTACGAAACTGACAG
AGGACAGATGGAACAAGCCCCAGAAGACCAAGGGCCACAGAGGGAGCCATACAATGAA
TGGACACTAGCATCGAT

FIGURE 15

Chim2 (SEQ ID NO: 13)

TATCGATGGGATTATGGAAAACAGATGGCAGGTGATGATTGTGTGGCAAGTAGACAGGATGAGGATTAACACATGGAAAA
GATTAGTAAAACACCATATGTATATTTCAAGGAAAGCTAAGGACTGGTTTTATAGACATCACTATGAAAGTACTAATCCA
AAAATAAGTTCAGAAGTACACATCCCACTAGGGGATGCTAAATTAGTAATAACAACATATTGGGGTCTGCATACAGGAGA
AAGAGACTGGCATTTGGGTCAGGGAGTCTCCATAGAatggaggaaaaagagatatagcacacaagtagaccctggcctag
cagaccaactaattcatcggtattattttgattgtttttcagaatctgctataagaaatgccatactaggaaatgtagtt
agacttagttgtgaatatcaagcaggacataacaagataggatctctacaatacttggcactagcagcattaataacacc
aaaaaagataaagccacctttgcctagtgttacgaaactgacagaggatagatggaacaagccccagaagaccaagggcc
acagaaggaaccatacaatgaatggacactagatcgatA (SEQ ID NO: 14)

ATCGATGGGATTATGGAAAACAGATGGCAGGTGATGATTGTGTGGCAAGTAGACAGGATGAGGATTAACACATGGAAAAG
ATTAGTAAAACACCATATGTATATTTCAAGGAAAGCTAAGGACTGGTTTTATAGACATCACTATGAAAGTACTAATCCAA
AAATAAGTTCAGAAGTACACATCCCACTAGGGGATGCTAAATTAGTAATAACAACATATTGGGGTCTGCATACAGGAGAA
AGAGACTGGCATTTGGGTCAGGGAGTCTCCATAGAATGGAGGAAAAAGAGATATAGCACACAAGTAGACCCTGGCCTAGC
AGACCAACTAATTCATCGGTATTATTTTGATTGTTTTTCAGAATCTGCTATAAGAAATGCCATACTAGGAAATGTAGTTA
GACTTAGTTGTGAATATCAAGCAGGACATAACAAGATAGGATCTCTACAATACTTGGCACTAGCAGCATTAATAACACCA
AAAAAGATAAAGCCACCTTTGCCTAGTGTTACGAAACTGACAGAGGATAGATGGAACAAGCCCCAGAAGACCAAGGGCCA
CAGAAGGAACCATACAATGAATGGACACTAGATCGATA

Figure 16

SEQ ID NO: 15

ATCGATGGGATTATGGAAAACAGATGGCAGGTGATGATTGTGTGGCAAGTAGACAGG
ATGAGGATTAACACATGGAAAAGATTAGTAAAACACCATATGTATATTTCAAGGAAAG
CTAAGGACTGGTTTTATAGACATCACTATGAAAGTACTAATCCAAAAATAAGTTCAGAA
GTACACATCCCACTAGGGGATGCTAAATTAGTAATAACAACATATTGGGGTCTGCATA
CAGGAGAAAGAGACTGGCATTTGGGTCAGGGAGTCTCCATAGAATGGAGGAAAAAGA
GATATAGCACACAAGTAGACCCTGACCTAGCAGACCAACTAATTCATCTGCACTATTT
TGATTGTTTTTCAGAATCTGCTATAAGAAATACCATATTAGGACGTATAGTTAGTCCTA
GGTGTGAATATCAAGCAGGACATAACAAGGTAGGATCTCTACAGTACTTGGCACTAG
CAGCATTAATAAAACCAAAACAGATAAAGCCACCTTTGCCTAGTGTTAGGAAACTGAC
AGAGGACAGATGGAACAAGCCCCAGAAGACCAAGGGCCACAGAGGGAGCCATACAA
TGAATGGACACTAGCATCGAT

Figure 17 - NL4-3

SEQ ID NO: 16

ATCGATGGGATTATGGAAAACAGATGGCAGGTGATGATTGTGTGGCAAGTAGACAGGAT
GAGGATTAGAACATGGATAAGTTTAGTAAAACACCATATATATATTTCAAAGAAAGCTAAG
GGATGGTTTTATAAACATCACTATGAAAGCACTAATCCAAGAATAAGTTCAGAAGTACACA
TCCCACTAGGGGATGCTAGATTGGTAGTAACAACATATTGGGGTCTGCATACAGGAGAA
AGAGACTGGAATTTAGGCCAGGGAGTCTCCATAGAATGGAGGAAAAAGAGATATAGCAC
ACAAGTAGACCCTGGCCTAGCAGACCAACTAATTCATCGGTATTATTTTGATTGTTTTTCA
GAATCTGCTATAAGAAATGCCATACTAGGAAATGTAGTTAGACTTAGTTGTGAATATCAAG
CAGGACATAACAAGATAGGATCTCTACAATACTTGGCACTAGCAGCATTAATAACACCAA
AAAAGATAAAGCCACCTTTGCCTAGTGTTACGAAACTGACAGAGGATAGATGGAACAAG
CCCCAGAAGACCAAGGGCCACAGAAGGAACCATACAATGAATGGACACTAG

Figure 18 F12-Vif

HIV VIF MUTANTS

FIELD OF THE INVENTION

The present invention relates to a lentiviral vector and its use in a method of imparting resistivity to infection by HIV, including superinfection by HIV.

BACKGROUND OF THE INVENTION

AIDS is one of the leading causes of death in the developing world, its spread reaching pandemic proportions. However, eradication of HIV-1 is far from being accomplished. Currently, the highly active anti-retroviral therapy (HAART) is the only efficacious treatment to reduce progression and spread of AIDS, although its long-term use is associated with drawbacks and limitations such as adherence to a complex dosing regimen, side effect toxicity and elevated cost (Richman et al., 2001). The great intra- and inter-subtype genetic and antigenic variability of HIV-1, stemming from the high mutation rate of its genome, together with inadequate compliance, is responsible for resistance to HAART drugs, as well as for the repeated failure in developing a multiple clades-based preventive vaccine (Ho et al., 2002). On this basis, development of alternative and/or additional therapeutic strategies against AIDS are mandatory.

Many years of pre-clinical investigation have shown that the HIV-1 life cycle can be interfered with at many levels, and proved at least the concept of anti-HIV gene therapy (Buchschacher et al., 2001). Hematopoietic stem cells (HSCs), T-cell precursors or T lymphocytes can be genetically modified with, for example, genes encoding ribozymes, decoys, antisense and small interfering RNA (siRNA) molecules directed against viral and cellular genes (Buchschacher et al., 2001; Jacque et al., 2002; Novina et al., 2002; Lee et al., 2002; Coburn et al., 2002; Qin et al., 2003), or proteins such as intrakines, toxins and single chain antibodies. However, early clinical trials with T lymphocytes transduced with retroviral vectors expressing transdominant mutants of viral proteins or anti-HIV-1 rybozimes have been disappointing (Woffendin et al., 1996; Ranga et al., 1998; Wong-Staal et al., 1998) mainly due to low gene transfer efficiency, insufficient engraftment and short in vivo persistence of the genetically modified T cells. Most of the pre-clinical and clinical studies carried out so far have been based on the use of retroviral vectors derived from the Moloney murine leukemia virus (MLV) to transduce HSCs or T-cells. However, MLV-derived vectors have shown major limitations for clinical applications, such as poor efficiency in transducing non-dividing HSCs and T-cells, insufficient expression of potentially therapeutic anti-HIV products, and propensity to induce neoplasia by insertional activation of oncogenes (Baum et al., 2003).

Among the possible targets of anti-HIV gene therapy is the product of the viral infectivity factor (vif) gene. vif is one of the 4 accessory genes of HIV-1, expressed at a late phase during virus replication in a Rev-dependent manner (Cullen et al., 1998; Frankel et al., 1998). The Vif protein is required for high viral infectivity in the so-called 'non-permissive' cells, which include the natural targets of HIV-1 (T-cells and macrophages) and some T-cell lines, for example, CEM, H9, and HUT 78 (Fisher et al., 1987; Fouchier et al., 1996; Gabuzda et al., 1992; Sheehy et al., 2002; Simon et al., 1996; von Schedler et al., 1993). This requirement depends on the ability of Vif to counteract the action of the recently identified CEM15/APOBEC-3G protein (Sheehy et al., 2002) which confers innate immunity to HIV-1. Thus, disabling, or interfering with, the function of Vif could represent an alternative anti-HIV-1 therapeutic approach.

F12-vif is a natural mutant of vif, carrying 15 unique amino acid substitutions, originally discovered in the F12 non-producer variant of HIV-1 (Federico et al., 1989; Carlini et al., 1992; Carlini et al., 1996). The F12 non-producer HIV induces a block in the replication of superinfecting HIV and F12-Vif may play a role in the reduced infectivity of this producer. However, there is a need to provide further vif mutants with anti-HIV activity, and to provide effective delivery systems for these mutants. The present invention seeks to overcome these problems.

SUMMARY OF THE INVENTION

We have developed novel mutants of vif that are highly effective in inhibiting HIV-1 replication in vitro in T cell lines infected with HIV-1. In particular, we have found that a Vif protein which comprises replacement amino acids at the amino acids corresponding to positions 127, 128, 130, 131, 132 and 142 of the wild-type sequence is sufficient for exerting antiviral effect against HIV. Moreover, we show that a 45 amino acid region of F12-Vif (Chim3), carrying only 6 unique amino acid substitutions, embedded in a WT-Vif context, protects human T-lymphocytes from HIV-1 infection. Furthermore, we show that in contrast to F12-Vif, Chim3 cannot rescue the replication of Vif deficient virions (Δvif HIV-1) in non-permissive cells, making the use of this mutant much safer in situations wherein it encounters Δvif HIV-1 quasispecies silently harboured in a patient.

An advantage associated with one embodiment of the present invention is that the mutant Vif transgene is under the transcriptional control of a Tat-dependent, wild-type HIV-1 LTR, which is activated only in HIV-1-infected cells, thus avoiding unnecessary expression of a foreign antigen in transduced HSCs and their progeny i.e., expression of HIV-1 is under HIV-1 inducible control.

STATEMENTS OF THE INVENTION

According to a first aspect of the present invention there is provided a polynucleotide comprising a nucleotide sequence encoding Vif wherein each of the amino acids corresponding to positions 127, 128, 130, 131, 132 and 142 of the sequence in FIG. 1A are replaced with another amino acid (i.e. the amino acids are not H, I, S, P, R and V respectively) and wherein the nucleotide sequence does not encode the amino acid sequence in FIG. 2.

According to another aspect of the present invention there is provided a polynucleotide comprising a nucleotide sequence encoding Vif wherein each of the amino acids corresponding to positions 127, 128, 130, 131, 132 and 142 of the sequence in FIG. 1A are replaced with another amino acid and wherein one or more of the amino acids corresponding to positions 22, 29, 41, 48, 66, 80, 109, 185 and 186 are not I, I, K, N, V, N, R, R and N respectively.

Preferably all of the amino acids corresponding to positions 22, 29, 41, 48, 66, 80, 109, 185 and 186 are not I, I, K, N, V, N, R, R and N respectively.

In one embodiment each of the amino acids corresponding to positions 127, 128, 130, 131, 132 and 142 of the sequence in FIG. 1A are replaced with another amino acid and all of the amino acids corresponding to positions 22, 29, 41, 66, 80, 109, 185 and 186 are not I, I, K, V, N, R, R and N respectively.

Preferably all of the amino acids corresponding to positions 127, 128, 130, 131, 132 and 142 are replaced with N, V, R, L, S and I respectively.

In one embodiment the amino acid corresponding to position 48 is N.

Preferably the amino acids corresponding to positions 22, 29, 41, 48, 66, 80, 109, 185 and 186 are those present in a naturally occurring Vif, such as, but not limited to, HXB2 acc. #K03455, BRU acc.# K02013, SF2 acc.# K02007, PV22 acc.# K02083, MN acc.#M17449 and NL4-3 acc. # M119921 (see FIGS. 1A, 1B and 1C). Suitable amino acids for these positions are, but not limited to, 22 (K), 29 (M), 41 (R), 48 (N or U), 66 (I), 80 (H), 109 (L), 185 (G), 186 (S).

According to another aspect of the present invention there is provided a polynucleotide comprising a nucleotide sequence encoding Vif wherein each of the amino acids corresponding to positions 127, 128, 130, 131, 132, 142 and 185 of the sequence in FIG. 1A are replaced with another amino acid (i.e. the amino acids are not H, I, S, P, R, V and G respectively) and wherein one or more of the amino acids corresponding to positions 22, 29, 41, 48, 66, 80, 109 and 186 are not I, I, K, N, V, N, R and N respectively.

Preferably all of the amino acids corresponding to positions 22, 29, 41, 48, 66, 80, 109 and 186 are not I, I, K, N, V, N, R and N respectively.

In one embodiment each of the amino acids corresponding to positions 127, 128, 130, 131, 132, 142 and 185 of the sequence in FIG. 1A are replaced with another amino acid and all of the amino acids corresponding to positions 22, 29, 41, 66, 80, 109 and 186 are not I, I, K, V, N, R and N respectively.

Preferably the amino acids corresponding to positions 127, 128, 130, 131, 132, 142 and 185 are replaced with N, V, R, L, S, I and R respectively.

In one embodiment the amino acid corresponding to position 48 is N.

Preferably the amino acids corresponding to positions 22, 29, 41, 48, 66, 80, 109 and 186 are those present in a naturally occurring Vif, such as, but not limited to, HXB2 acc. #K03455, BRU acc.# K02013, SF2 acc.# K02007, PV22 acc.# K02083, MN acc.#M17449 and NL4-3 acc. # M19921 (see FIGS. 1A, 1B and 1C). Suitable amino acids for these positions are, but not limited to, 22 (K), 29 (M), 41 (R), 48 (N or H), 66 (I), 80 (H), 109 (L), 186 (S).

According to another aspect of the present invention there is provided a polynucleotide comprising a nucleotide sequence encoding Vif wherein each of the amino acids corresponding to positions 127, 128, 130, 131, 132, 142, 185 and 186 of the sequence in FIG. 1A are replaced with another amino acid (i.e. the amino acids are not H, I, S, P, R, V, G or S respectively) and wherein one or more of the amino acids corresponding to positions 22, 29, 41 48, 66, 80 and 109 are not I, I, K, N, V, N and R respectively.

Preferably all of the amino acids corresponding to positions 22, 29, 41 48, 66, 80 and 109 are not I, I, K, N, V, N and R respectively.

In one embodiment each of the amino acids corresponding to positions 127, 128, 130, 131, 132, 142, 185 and 186 of the sequence in FIG. 1A are replaced with another amino acid and all of the amino acids corresponding to positions 22, 29, 41, 66, 80 and 109 are not I, I, K, V, N and R respectively.

Preferably the amino acids corresponding to positions 127, 128, 130, 131, 132, 142, 185 and 186 are replaced with N, V, R, L, S, I, R and N respectively.

In one embodiment the amino acid corresponding to position 48 is N.

Preferably the amino acids corresponding to positions 22, 29, 41, 48, 66, 80, 109 are those present in a naturally occurring Vif, such as, but not limited to, HXB2 acc. #K03455, BRU acc.# K02013, SF2 acc.# K02007, PV22 acc.# K02083, MN acc.#M17449 and NL4-3 acc. # M19921 (see FIGS. 1A, 1B and 1C). Suitable amino acids for these positions are, but not limited to, 22 (K), 29 (M), 41 (R), 48 (N or H), 66 (1), 80 (H), 109.

According to another aspect of the present invention there is provided a polynucleotide comprising a nucleotide sequence encoding Vif wherein each of the amino acids corresponding to positions 109, 127, 128, 130, 131, 132, 142, 185 and 186 of the sequence in FIG. 1A are replaced with another amino acid (i.e. the amino acids are not L, H, I, S, P, R, V, G or S respectively) and wherein one or more of the amino acids corresponding to positions 22, 29, 41, 48, 66 and 80 are not I, I, K, N, V and N respectively.

Preferably all of the amino acids corresponding to positions 22, 29, 41, 48, 66 and 80 are not I, I, K, N, V and N respectively.

In one embodiment each of the amino acids corresponding to positions 109, 127, 128, 130, 131, 132, 142, 185 and 186 of the sequence in FIG. 1A are replaced with another amino acid and all of the amino acids corresponding to positions 22, 29, 41, 66 and 80 are not I, I, K, V and N respectively.

Preferably the amino acids corresponding to positions 109, 127, 128, 130, 131, 132, 142, 185 and 186 are replaced with R, N, V, R, L, S, I, R and N respectively.

In one embodiment the amino acid corresponding to position 48 is N.

Preferably the amino acids corresponding to positions 22, 29, 41, 48, 66, 80 are those present in a naturally occurring Vif, such as, but not limited to, HXB2 acc. #K03455, BRU acc.# K02013, SF2 acc.# K02007, PV22 acc.#K02083, MN acc.#M17449 and NL4-3 acc. # M19921 (see FIGS. 1A, 1B and 1C). Suitable amino acids for these positions are, but not limited to, 22 (K), 29 (M), 41 (R), 48 (N or H), 66 (I), 80 (H).

According to another aspect of the present invention there is provided a polynucleotide comprising a nucleotide sequence encoding Vif wherein each of the amino acids corresponding to positions 80, 109, 127, 128, 130, 131, 132, 142, 185 and 186 of the sequence in FIG. 1A are replaced with another amino acid (i.e. the amino acids are not H, L, H, I, S, P, R, V, G and S respectively) and wherein one or more of the amino acids corresponding to positions 22, 29, 41, 48 and 66 are not I, I, K, N and V respectively.

Preferably all of the amino acids corresponding to positions 22, 29, 41, 48 and 66 are not I, I, K, N and V respectively.

In one embodiment each of the amino acids corresponding to positions 80, 109, 127, 128, 130, 131, 132, 142, 185 and 186 of the sequence in FIG. 1A are replaced with another amino acid and all of the amino acids corresponding to positions 22, 29, 41, and 66 are not I, I, K and V respectively.

Preferably the amino acids corresponding to positions 80, 109, 127, 128, 130, 131, 132, 142, 185 and 186 are replaced with N, R, N, V, R, L, S, I, R and N respectively.

In one embodiment the amino acid corresponding to position 48 is N.

Preferably the amino acids corresponding to positions 22, 29, 41, 48 and 66 are those present in a naturally occurring Vif, such as, but not limited to, HXB2 acc. #K03455, BRU acc.# K02013, SF2 acc.# K02007, PV22 acc.# K02083, MN acc.#M17449 and NL4-3 acc. # M19921 (see FIGS. 1A, 1B, and 1C). Suitable amino acids for these positions are, but not limited to, 22 (K), 29 (M), 41 (R), 48 (N or H), 66 (I).

According to another aspect of the present invention there is provided a polynucleotide comprising a nucleotide sequence encoding Vif wherein each of the amino acids corresponding to positions 66, 80, 109, 127, 128, 130, 131, 132, 142, 185 and 186 of the sequence in FIG. 1A are replaced with another amino acid (i.e. the amino acids are not I, H, L, H, I, S, P, R, V, G and S respectively) and wherein one or more of the amino acids corresponding to positions 22, 29, 41 and 48 are not I, I, K and N respectively.

Preferably all of the amino acids corresponding to positions 22, 29, 41 and 48 are not I, I, K and N respectively.

In one embodiment each of the amino acids corresponding to positions 66, 80, 109, 127, 128, 130, 131, 132, 142, 185 and 186 of the sequence in FIG. 1A are replaced with another amino acid and all of the amino acids corresponding to positions 22, 29 and 41 are not I, I and K respectively.

Preferably the amino acids corresponding to positions 66, 80, 109, 127, 128, 130, 131, 132, 142, 185 and 186 are replaced with V, N, R, N, V, R, L, S, I, R and N respectively.

In one embodiment the amino acid corresponding to position 48 is N.

Preferably the amino acids corresponding to positions 22, 29, 41 and 48 are those present in a naturally occurring Vif, such as, but not limited to, HXB2 acc. #K03455, BRU acc.# K02013, SF2 acc.# K02007, PV22 acc.# K02083, MN acc.#M17449 and NL4-3 acc. # M19921 (see FIGS. 1A, 1B and 1C). Suitable amino acids for these positions are, but not limited to, 22 (K), 29 (M), 41 (R), 48 (N, H).

According to another aspect of the present invention there is provided a polynucleotide comprising a nucleotide sequence encoding Vif wherein each of the amino acids corresponding to positions 48, 66, 80, 109, 127, 128, 130, 131, 132, 142, 185 and 186 of the sequence in FIG. 1A are replaced with another amino acid (i.e. the amino acids are not H, I, H, L, H, I, S, P, R, V, G and S respectively) and wherein one or more of the amino acids corresponding to positions 22, 29 and 41 are not I, I and K respectively.

Preferably all of the amino acids corresponding to positions 22, 29 and 41 are not I, I and K respectively.

Preferably the amino acids corresponding to 48, 66, 80, 109, 127, 128, 130, 131, 132, 142, 185 and 186 are replaced with N, V, N, R, N, V, R, L, S, I, R and N respectively.

Preferably the amino acids corresponding to positions 22, 29 and 41 are those present in a naturally occurring Vif, such as, but not limited to, HXB2 acc. #K03455, BRU acc.# K02013, SF2 acc.# K02007, PV22 acc.# K02083, MN acc.#M17449 and NL4-3 ace. # M19921 (see FIGS. 1A, 1B and 1C). Suitable amino acids for these positions are, but not limited to, 22 (E), 29 (M), 41 (R).

According to another aspect of the present invention there is provided a polynucleotide comprising a nucleotide sequence encoding Vif wherein each of the amino acids corresponding to positions 41, 48, 66, 80, 109, 127, 128, 130, 131, 132, 142, 185 and 186 of the sequence in FIG. 1A are replaced with another amino acid (i.e. the amino acids are not R, H, I, H, L, H, I, S, P, R, V, G and S respectively) and wherein at least one of the amino acids corresponding to position 22 and 29 is not I.

Preferably the amino acids corresponding to 41, 48, 66, 80, 109, 127, 128, 130, 131, 132, 142, 185 and 186 are replaced with K, N, V, N, R, N, V, R, L, S, I, R and N respectively.

Preferably the amino acids corresponding to positions 22 and 29, are those present in a naturally occurring Vif, such as, but not limited to, HXB2 acc. #K03455, BRU acc.# K02013, SF2 acc.# K02007, PV22 acc.# K02083, MN acc.#M17449 and NL4-3 acc. # M19921 (see FIGS. 1A, 1B and 1C). Suitable amino acids for these positions are, but not limited to, 22 (K), 29 (M).

Preferably both of the amino acids corresponding to position 22 and 29 are not I.

According to another aspect of the present invention there is provided a polynucleotide comprising a nucleotide sequence encoding Vif wherein each of the amino acids corresponding to positions 29, 41, 48, 66, 80, 109, 127, 128, 130, 131, 132, 142, 185 and 186 of the sequence in FIG. 1A are replaced with another amino acid (i.e. the amino acids are not M, R, H, I, H, L, H, I, S, P, R, V, G and S respectively) and the amino acid corresponding to position 22 is not I.

Preferably the amino acids corresponding to positions 29, 41, 48, 66, 80, 109, 127, 128, 130, 131, 132, 142, 185 and 186 are replaced with I, K, N, V, N, R, N, V, R, L, S, I, R and N respectively.

Preferably the amino acid corresponding to position 22 is that present in a naturally occurring Vif, such as, but not limited to, HXB2 acc. #K03455, BRU acc.# K02013, SF2 acc.# K02007, PV22 acc.# K02083, MN acc.#M17449 and NL4-3 acc. # M19921 (see FIGS. 1A, 1B and 1C). A Suitable amino acid for this position is, but not limited to, K (Lysine).

According to another aspect of the present invention there is provided a polynucleotide comprising the nucleotide sequence encoding a chimeric Vif protein comprising amino acids 126 to 170 of the F12-Vif sequence in FIG. 2 embedded in a naturally occurring Vif sequence, such as, but not limited to, HXB2 acc. #K03455, BRU acc.# K02013, SF2 acc.# K02007, PV22 acc.# K02083, MN acc.#M17449 and NL4-3 ace. # M19921 (see FIGS. 1A, 1B, 1C and 2). In this regard, the naturally occurring Vif sequence is not F12-Vif.

According to another aspect of the present invention there is provided a polynucleotide comprising a nucleotide sequence encoding a fragment of the Vif polypeptide as defined above wherein the fragment comprises at least amino acids corresponding to 126 to 170 of the sequence in FIG. 2.

Preferably the fragment comprises at least amino acids 126 to 170 of the sequence in FIG. 2.

In one embodiment the fragment consists of amino acids 126 to 170 of the sequence in FIG. 2.

According to another aspect of the present invention there is provided a polynucleotide comprising a nucleotide sequence encoding a fragment of Vif polypeptide wherein said fragment comprises replacement amino acids at the amino acids corresponding to positions 127, 128, 130, 131, 132 and 142 of the wild-type sequence in FIG. 1A.

In one embodiment, the fragment encoded by the polynucleotide further comprises a replacement amino acid at the amino acid corresponding to position 185 of the wild-type sequence in FIG. 1A.

In another embodiment, the fragment encoded by the polynucleotide further comprises a replacement amino acid at the amino acid corresponding to position 186 of the wild-type sequence in FIG. 1A.

In another embodiment, the fragment encoded by the polynucleotide further comprises a replacement amino acid at the amino acid corresponding to position 109 of the wild-type sequence in FIG. 1A.

In another embodiment, the fragment encoded by the polynucleotide further comprises a replacement amino acid at the amino acid corresponding to position 80 of the wild-type sequence in FIG. 1A.

In another embodiment, the fragment encoded by the polynucleotide further comprises a replacement amino acid at the amino acid corresponding to position 66 of the wild-type sequence in FIG. 1A.

In another embodiment, the fragment encoded by the polynucleotide further comprises a replacement amino acid at the amino acid corresponding to position 48 of the wild-type sequence in FIG. 1A.

In another embodiment, the fragment encoded by the polynucleotide further comprises a replacement amino acid at the amino acid corresponding to position 41 of the wild-type sequence in FIG. 1A.

In another embodiment, the fragment encoded by the polynucleotide further comprises a replacement amino acid at the amino acid corresponding to position 29 of the wild-type sequence in FIG. 1A.

Preferably the amino acid at position 22 of the wild-type sequence in FIG. 1A is altered to I.

Preferably the amino acid at position 29 of the wild-type sequence in FIG. 1A is altered to I.

Preferably the amino acid at position 41 of the wild-type sequence in FIG. 1A is altered to K.

Preferably the amino acid at position 48 of the wild-type sequence in FIG. 1A is altered to N.

Preferably the amino acid at position 66 of the wild-type sequence in FIG. 1A is altered to V Preferably the amino acid at position 80 of the wild-type sequence in FIG. 1A is altered to N.

Preferably the amino acid at position 109 of the wild-type sequence in FIG. 1A is altered to R.

Preferably the amino acid at position 127 of the wild-type sequence in FIG. 1A is altered to N.

Preferably the amino acid at position 128 of the wild-type sequence in FIG. 1A is altered to V.

Preferably the amino acid at position 130 of the wild-type sequence in FIG. 1A is altered to R.

Preferably the amino acid at position 131 of the wild-type sequence in FIG. 1A is altered to L.

Preferably the amino acid at position 132 of the wild-type sequence in FIG. 1A is altered to S.

Preferably the amino acid at position 142 of the wild-type sequence in FIG. 1A is altered to I.

Preferably the amino acid at position 185 of the wild-type sequence in FIG. 1A is altered to R.

Preferably the amino acid at position 186 of the wild-type sequence in FIG. 1A is altered to N.

According to another aspect of the present invention there is provided a polynucleotide consisting of or comprising a nucleotide sequence encoding the amino acid sequence shown in FIG. 4A.

According to another aspect of the present invention there is provided a polynucleotide consisting of or comprising a nucleotide sequence encoding the amino acid sequence shown in FIG. 5A.

According to another aspect of the present invention there is provided a polynucleotide consisting of or comprising a nucleotide sequence as shown in FIG. 15 or 16.

According to another aspect of the present invention there is provided Vif polypeptides and Vif polypeptide fragments encoded by the polynucleotides of the present invention.

According to another aspect of the present invention there is provided a polypeptide comprising or consisting of the amino acid sequence shown in FIG. 4A or 4B.

According to another aspect of the present invention there is provided a vector comprising a polynucleotide of the present invention.

Preferably, the vector is a recombinant lentiviral vector.

Preferably, the lentiviral vector is derivable from HIV.

Preferably, the vector encodes a polynucleotide of the present invention which is operably linked to a viral LTR.

Preferably the expression of the polynucleotide is tat and rev dependent.

Preferably the vector of the present invention does not comprise the tat and rev genes.

Preferably the vector of the present invention is capable of expressing the mutant Vif or mutant Vif fragment under HIV-1 inducible control.

Preferably the vector of the present invention lacks the gag, pol and env genes.

In one embodiment, the vector of the present invention further comprises a polynucleotide sequence encoding a selection marker gene.

Preferably the vector of the present invention further comprises a polynucleotide sequence encoding at least part of the low affinity nerve growth factor receptor (LNGFR).

In another embodiment, the vector of the present invention is in the form of an integrated provirus.

According to another aspect of the present invention there is provided a retroviral particle obtainable from the vector of the present invention.

Preferably the retroviral particle is pseudotyped.

Preferably the polynucleotide encoding the mutant Vif is operably linked to a viral long terminal repeat (LTR).

According to another aspect of the present invention there is provided a retroviral production system for producing the retroviral particle of the present invention comprising the vector of the present invention and retroviral gag-pol and retroviral or non retroviral env. In particular, the concept of pseudotyping is well known in the art and may be used in the present invention.

Preferably the retroviral gag-pol and env are on different vectors.

Preferably the envelope protein is selected from the group consisting of RD114-TR, VSV-G, GALV and 4070A.

According to another aspect of the present invention there is provided cell comprising a polynucleotide of the present invention.

According to another aspect of the present invention there is provided a cell infected or transduced with a vector or the retroviral particle of the present invention.

Preferably the cell is a T-cell.

Preferably the cell is a monocyte, macrophage or lymphocyte.

Preferably the cell is a hematopoietic CD34+ precursor cell or a hematopoietic cell.

Preferably the cell of the present invention expresses mutant Vif under HIV-1 inducible control.

According to another aspect of the present invention there is provided a polynucleotide, a polypeptide, a vector, a retroviral particle or a cell of the present invention for use in medicine.

According to another aspect of the present invention there is provided a pharmaceutical composition comprising a polynucleotide, a polypeptide, a vector, a retroviral particle or a cell of the present invention and a pharmaceutically acceptable carrier, diluent or excipient.

According to another aspect of the present invention there is provided use of a polynucleotide, a polypeptide, a vector, a retroviral particle, a cell or a pharmaceutical composition of the present invention for the preparation of a medicament for treatment or prevention of HIV infection or related conditions. The HIV infection may represent superinfection.

Thus, the present invention provides a method of treating or preventing HIV infection or related conditions comprising administering to a patient in need of the same an effective amount of a polypeptide, a polynucleotide, a vector, a retroviral particle, a cell or a pharmaceutical composition of the present invention.

According to a further aspect of the present invention there is provided a method of treating or preventing HIV infection or a related condition comprising infecting or transducing a cell with a vector or a retroviral particle of the present invention In one embodiment the infecting or transducing is carried out ex vivo and the cell is introduced in a patient.

DESCRIPTION OF THE FIGURES

FIG. 1A shows the consensus WT amino acid sequence (SEQ ID NO: 1) generated by 5 amino acid sequences of Vif (HXB2 acc.# K03455, BRU acc.# K02013, SF2 acc.# K02007, PV22 acc.# K02083, MN acc.# M17449). The accession numbers refer to NCBI Genbank accession numbers FIG. 1B shows the alignment of the 5 amino acid sequences of Vif (SEQ ID NOs: 2, 3, 4, 5 and 6), the consensus sequence generated (SEQ ID NO: 1) and the F12-Vif sequence (SEQ ID NO: 7).

FIG. 1C shows the WT Vif amino acid sequence of NL4-3 (SEQ ID NO: 8).

FIG. 2 shows the HIV F12-Vif polypeptide sequence (NCBI accession number: Z11530) (SEQ ID NO: 7) from HIV1 F12. The unique amino acid substitutions are shown in bold.

FIG. 3A shows the Chim1 polypeptide sequence (SEQ ID NO: 9). Amino acids in bold represent replacement amino acids relative to wild type Vif (NL4-3).

FIG. 3B highlights the portions of Chim 1 (SEQ ID NO: 9) that correspond to F12-Vif (italics) and to wild type Vif.

FIG. 4A shows the Chim2 polypeptide sequence (SEQ ID NO: 10). Amino acids in bold represent replacement amino acids relative to wild type Vif (NL4-3).

FIG. 4B highlights the portions of Chim 2 (SEQ ID NO: 10) that correspond to F12-Vif (italics) and to wild type Vif.

FIG. 5A shows the Chim3 polypeptide sequence (SEQ ID NO: 11). Amino acids in bold represent replacement amino acids relative to wild type Vif (NL4-3).

FIG. 5B highlights the portions of Chim 3 (SEQ ID NO: 11) that correspond to F12-Vif (italics) and to wild type Vif.

FIG. 6 shows a schematic representation of the HIV-1-based PΔN, WT-VifPΔN, F12-VifPΔN, Chim1-PΔN, Chim2-PΔN and Chim3-PΔN lentiviral vectors in their proviral form.

FIG. 15 shows the Chim3 polynucleotide sequence (SEQ ID NO: 12).

FIG. 16 shows Chim2 polynucleotide sequences (SEQ ID NO: 13).

FIG. 17 shows the WT Vif polynucleotide sequence of NL4-3 (SEQ ID NO: 15).

FIG. 18 shows F12-Vif polynucleotide sequence (SEQ ID NO: 16).

DETAILED DESCRIPTION

Figure 7:
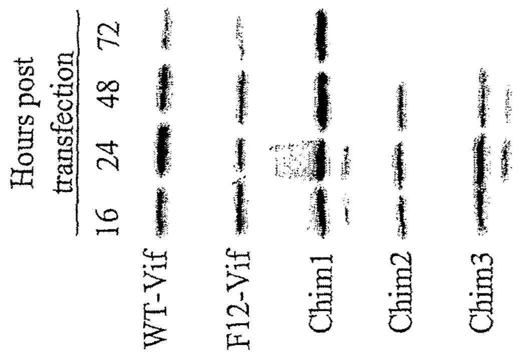
FIG. 7 shows analysis of the expression of Chim1, Chim2 and Chim3 in comparison with the WT- and F12-Vif full-length proteins by western blot assay.

Various preferred features and embodiments of the present invention will now be described by way of non-limiting example.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, Jolm Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Target Cell

The polypeptides, polynucleotides, vectors, retroviral particles, cells or pharmaceutical compositions of the present invention may be delivered to a target cell. Preferably, the cell is a cell of the immune system, e.g., a T-cell. Preferably the cell is a cell of the human immune system. Even more preferably the cell is a cell which is capable of being infected by HIV, i.e. an HIV permissive cell. Cells into which the recombinant lentiviral vector or particle of the present invention may be introduced include peripheral blood lymphocytes, monocytes, macrophages, astrocytes.

Viral Infectivity Factor (Vif)

It should be noted that in this application amino acid positions are identified by those 'corresponding' to a particular position in the consensus sequence of FIG. 1A. This is not to be interpreted as meaning the sequences of the present invention must include sequences present in FIG. 1A. A skilled person will readily appreciate that Vif sequences vary among different HIV strains. Reference to this figure is used merely to enable identification of a particular amino acid location within any particular Vif protein. Such amino acid locations can be routinely identified using sequence alignment programs, the use of which are well known in the art.

Lentiviruses such as HIV-1 encode a number of accessory genes in addition to the structural gag, pol, and env genes that are expressed by all replication-competent retroviruses. One of these accessory genes, vif (viral infectivity factor), is expressed by all known lentiviruses except equine infectious anemia virus. Vif protein is a highly basic, 23-kDa protein composed of 192 amino acids. Sequence analysis of viral DNA from HIV-1-infected-individuals has revealed that the open reading frame of Vif remains intact. (Sova, et al., 1995; Wieland et al., 1994; Wieland et al., 1997). In relatively native conditions, Vif proteins form multimers in vitro, including dimers, trimers or tetramers. It has also been demonstrated that Vif proteins may interact with each other within a cell. Further studies have indicated that the domain affecting Vif self-association is located at the C-terminus of this protein, especially the proline-enriched 151-164 region (Yang et al., 2001).

Deletion of the vif gene dramatically decreases the replication of simian immunodeficiency virus (SIV) in macaques and HIV-1 replication in SCID-hu mice (Aldrovandi, G. M. & Zack, J. A., J. Virol. 70:1505-1511, 1996; Desrosiers, R. C., et al., J. Virol. 72:1431-1437, 1998), indicating that it is essential for the pathogenic replication of lentiviruses in vivo. Previous findings have supported a role of Vif in proviral DNA integration (Simon et al., 1996; von Schwedler et al., 1993; Sova et al., 2001). It has also been shown that Vif interacts with either the genomic RNA (Zhang et al., 2000; Dettenhofer et al., 2000) or viral and cellular proteins such as the HP-68-Gag complex, which is involved in the late phase of capsid assembly (Zimmerman et al., 2002).

Vif-enhanced infectivity is conferred in the virus-producing cell yet only manifests itself in the target cell. vif proviruses can therefore be complimented in trans in virus-producing cells but not in target cells. Furthermore, the requirement for Vif is cell type-specific. The vif$^-$ viruses exhibit a negative phenotype when produced from primary T-lymphocytes, terminally differentiated macrophages, or a few T-lymphoid cell lines, such as H9. These cells are referred to as "nonpermissive" cells. In some T-cell lines such as SupT1, C8166, and other non-T-cells such as HelaCD4 cells, however, productive replication of vif$^-$ HIV-1 viruses can be achieved. These cell lines are referred to as "permissive" cells (Gabuzda et al., 1992; von Schwedler et al., 1993; Gabuzda et al., 1994). This requirement depends on the ability of Vif to counteract the action of the recently identified CEM15/APOBEC-3G protein (Sheehy et al., 2002) which is selectively expressed in non-permissive cells, and which confers innate immunity to HIV-1. APOBEC-3G is a cytidine deaminase cell protein incorporated into the vif deficient virions (Δvif HIV-1) during viral production, which induces massive G-to-A hyper mutation in the nascent plus strand cDNA during reverse transcription in infected cells leading to a strong inhibition of Δvif HIV-1 variant replication (Lecossier et al., 2003; Harris et al., 2003; Mariani et al., 2003; Goff et al., 2003). While the original founding member of the gene family, APOBEC, acts on RNA and deaminates only a single cytosine residue in its target apolipoprotein B mRNA to regulate its expression (Teng et al., 1998), APOBEC-3G is instead active on single-stranded DNA and is much more potent. As a result of its activity, about 1% to-2% of all the cytosine residues in the viral DNA are converted to uracil. After the attack by APOBEC-3G, deamination either generates a highly mutated DNA incapable of viral expansion or, by triggering a uracil-based excision pathway, prevents the accumulation of cDNA into target cells. Alternatively, the increased number of uracils in the minus strand could impair the initiation of plus-strand synthesis.

The mechanism of action by which Vif blocks APOBEC-3G is not yet completely clear. However, it has been shown that Vif significantly reduces the level of APOBEC-3G protein encapsulated in virons. To exclude APOBEC-3G from virions, Vif could mask the domain of APOBEC-3G that interacts with the assembling virions; could direct APOBEC-3G away from the site in the cell where the virus assembles; or could induce APOBEC-3G degradation. There is evidence to suggest that the major role of Vif is to induce the proteasome-dependent degradation of APOBEC3G and thereby to allow HIV-1 replication (Navarro et al., 2004; Trono, 2004). Degradation of APOBEC-3G is secondary to its ubiquitination by Vif, which forms a functional bridge between APOBEC-3G and an E3 ubiquitin ligase complex through the C-terminal SOCS box (Addo et al., 2003, and Harris et al., 2003).

The expression of viral components, including viral proteins and nucleic acids, is not altered in the virions produced from nonpermissive cells. (Fouchier et al., 1996; Gabuzda et al., 1992; von Schwedler et al., 1993). Deletion of the vif gene, however, results in alterations of virion morphology (Borman et al., 1995; Bouyac et al 1997; Hoglund et al., 1994).

A natural mutant of Vif (F12-Vif), carrying 15 unique amino acid substitutions, originally identified in the F12 HIV-1 variant (Federico et al., 1989), a non-producer provirus cloned from HUT 78 cells infected with a primary HIV-1 isolate shows anti-HIV-1 activity (D'Aloja et al., 1998).

We have developed novel mutants of vif that are highly effective in inhibiting HIV-1 replication in vitro in T cell lines infected with HIV-1. More specifically, we have found that the full-length sequence of F12-Vif is not necessary to protect against HIV infection. Indeed, we have shown that a 45 amino acid region of F12-Vif (F12-Vif-Chim3), carrying only 6 unique amino acid substitutions, embedded in a WT-Vif context, protects human T-lymphocytes from HIV-1 infection.

In various aspects of the present invention, the Vif protein may be a chimer of F12-Vif and a second Vif protein, the second Vif protein preferably being a naturally occurring Vif protein. For example, the second Vif protein may be HXB2 acc. #K03455, BRU acc.# K02013, SF2 acc.# K02007, PV22 acc.# K02083, MN acc.#M17449 or NL4-3 acc. # M19921 Vif (see FIGS. 1A, 1B and 1C). In one embodiment the second Vif protein used to make the chimer has none of the conserved 15 amino acid substitutions (i.e. at positions 22, 29, 41, 48, 66, 80, 109, 127, 128, 130, 131, 132, 142, 185 and 186) present in F12-Vif. Preferably the portions of the chimer which requires the F12-Vif specific substitutions are derived from the F12-Vif protein, the remainder being derived from the second Vif protein. For example, if F12-Vif specific substitutions are required at positions 127, 128, 130, 131, 132 and 142 (that is to say the amino acids at these points are N, V, R, L, S and I respectively), but not at positions 22, 29, 41, 48, 66, 80, 109, 185 and 186, then the portion of the chimer comprising at least amino acids 22 to 186 may be derived from F12-Vif, the remainder being derived form the second Vif protein.

In various aspects of the present invention, the Vif protein of the present invention may be produced by making point mutations at the required amino acids positions. For example, if F12-Vif specific substitutions are required at positions 127, 128, 130, 131, 132 and 142 (that is to say the amino acids at these points are N, V, R, L, S and I respectively), then such site-specific mutations (e.g. using the PCR overlapping technique (Taddeo et al., 1996)) may introduced to a naturally occurring Vif (e.g. NL4-3) at these positions.

Preferably the Vif protein of the present invention is a mutated Vif protein or fragment thereof, which when expressed in target cells, reduces or inhibits replication of HIV-1. The mutant Vif of the present invention may be mutated using standard mutagenesis techniques. By mutagenesis we also include deletion or substitution. In a particularly preferred embodiment, site-specific mutations are introduced using the PCR overlapping technique (Taddeo et al., 1996). The ability of mutant Vif to impart at least some resistance or super-resistance to HIV infection may be determined by analysing viral replication. Such assays are known to those skilled in the art and are described in D'Aloja 2001. Alternatively a mutant HIV Vif may be reverted to wild-type and the resulting products transfected into HIV-permissible cells. Such a method would enable the identification of further useful mutations thereby enabling the identification of further mutants useful in the present invention.

HIV

As used herein HIV encompasses all designations assigned to those viruses implicated as causative agents of acquired immunodeficiency syndrome (AIDS) and AIDS-related complex (ARC), such as HIV, e.g. HIV-1 and HIV-2, and HTLV, e.g. HTLV-III. Of the two major HIV types, HIV-1 and HIV-2, HIV-1 is the predominant species around the world. To date, two major groups of HIV-1 exist, "M" and "0". The viruses which cause the great majority of HIV-1 infections are in the M group. The 0 group isolates are genetically quite distant from the M group. HIV-1 subtypes of the M group include subtypes A-J.

Polynucleotides

Polynucleotides of the present invention may comprise DNA or RNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, male nucleotide substitutions that do not affect the polypeptide sequence encoded by the polynucleotides used in the invention to reflect the codon usage of any particular host organism in which the polypeptides are to be expressed. The polynucleotides may be modified by any method available in the art. Such modifications may be carried out in order to enhance the in vivo activity or life span of polynucleotides of the invention.

Polynucleotides such as DNA polynucleotides may be produced recombinantly, synthetically, or by any means available to those of skill in the art. They may also be cloned by standard techniques.

Longer polynucleotides will generally be produced using recombinant means, for example using PCR (polymerase chain reaction) cloning techniques. This will involve making a pair of primers (e.g. of about 15 to 30 nucleotides) flanking a region of the DNA targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Protein

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds. The terms subunit and domain may also refer to polypeptides and peptides having biological function.

Variants, Derivatives, Analogues, Homologues and Fragments

In addition to the specific proteins and nucleotides mentioned herein, the present invention also encompasses variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question retains at least one of its endogenous functions. A variant sequence can be modified by addition, deletion, substitution modification replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins of the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the transport or modulation function is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Polynucleotide variants will preferably comprise codon optimised sequences. Codon optimisation is known in the art as a method of enhancing RNA stability and therefor gene expression. The redundancy of the genetic code means that several different codons may encode the same amino-acid. For example, Leucine, Arginine and Serine are each encoded by six different codons. Different organisms show preferences in their use of the different codons. Viruses such as HIV, for instance, use a large number of rare codons. By changing a nucleotide sequence such that rare codons are replaced by the corresponding commonly used mammalian codons, increased expression of the sequences in mammalian target cells can be achieved. Codon usage tables are known in the art for mammalian cells, as well as for a variety of other organisms. Preferably, at least part of the sequence is codon optimised. Even more preferably, the sequence is codon optimised in its entirety.

Vectors

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences used in the invention and/or expressing the proteins used in the invention. Examples of vectors used in recombinant DNA techniques include but are not limited to plasmids, chromosomes, artificial chromosomes or viruses.

Polynucleotides of the invention are preferably incorporated into a vector. Preferably, the polynucleotide is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under conditions compatible with the control sequences.

The control sequences may be modified, for example by the addition of further transcriptional regulatory elements to make the level of transcription directed by the control sequences more responsive to transcriptional modulators.

The vectors of the present invention may be for example, plasmid or virus vectors provided with an origin of replication, optionally a promoter for the expression of a polynucleotide and optionally a regulator of the promoter. The vectors may contain one or more selectable marker genes, and/or a traceable marker such as GFP. Vectors may be used, for example, to transfect or transform a host cell.

Control sequences operably linked to sequences encoding proteins of the present invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

The vector of the present invention may be a retrovirus based vector which has been genetically engineered so that it can not replicate and produce progeny infectious virus particles once the virus has entered the target cell.

Retroviruses

A large number of different retroviruses have been identified. Examples include: murine leukemia virus (MLV), human immunodeficiency virus (HIV), simian immunodeficiency virus, human T-cell leukemia virus (HTLV). equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "Retroviruses", Cold Spring Harbour Laboratory Press Eds: J M Coffin, S M Hughes, H E Varmus pp 758-763.

Details on the genomic structure of some retroviruses may be found in the art. By way of example, details on HIV and Mo-MLV may be found from the NCBI Genbank (Genome Accession Nos. AF033819 and AF033811, respectively).

Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al., 1997 (ibid).

Each retroviral genome comprises genes called gag, pol and env which code for virion proteins and enzymes. In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

The basic molecular organisation of an infectious retroviral RNA genome is (5') R-U5-gag, pol, env-U3-R (3'). In a defective retroviral vector genome gag, pol and env may be absent or not functional. The R regions at both ends of the RNA are repeated sequences. U5 and U3 represent unique sequences at the 5' and 3' ends of the RNA genome respectively.

Host range and tissue tropism varies between different retroviruses. In some cases, this specificity may restrict the transduction potential of a recombinant retroviral vector. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types.

In some cases however, it may be beneficial, especially from a safety point of view, to target specifically restricted cells. Replacement of the env gene with a heterologous env gene is an example of a technique or strategy used to target specifically certain cell types. This technique is called pseudotyping.

The term "recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV in use typically carries non-viral coding sequences which are to be delivered by the vector to the target cell. An RRV is incapable of independent replication to produce infectious retroviral particles within the final target cell. The "recombinant retroviral vector" of the present invention is derived from a lentiviral vector. Put another way, the recombinant retroviral vector of the present invention is a "recombinant lentiviral vector".

In a typical recombinant retroviral vector for use in gene therapy, at least part of one or more of the gag, pot and env protein coding regions essential for replication may be removed from the virus. This makes the retroviral vector replication-defective. The removed portions may then be replaced by the polynucleotide of the present invention to generate a virus capable of integrating its genome into a host genome but wherein the modified viral genome is unable to propagate itself due to a lack of structural proteins. When integrated in the host genome, expression of the polynucleotide occurs—resulting in, for example, a therapeutic and/or a diagnostic effect. Thus, the transfer of a polynucleotide into a site of interest is typically achieved by: integrating the polynucleotide into the recombinant viral vector; packaging the modified viral vector into a virion coat; and allowing transduction of a target cell.

Replication-defective retroviral vectors are typically propagated, for example to prepare suitable titres of the retroviral vector for subsequent transduction, by using a combination of a packaging or helper cell line and the recombinant vector. That is to say, that the three packaging proteins can be provided in trans.

A "packaging cell line" contains one or more of the retroviral gag, pot and env genes. The packaging cell line produces the proteins required for packaging retroviral DNA but it cannot bring about encapsidation due to the lack of a psi region. However, when a recombinant vector carrying a polynucleotide and a psi region is introduced into the packaging cell line, the helper proteins can package the psi-positive recombinant vector to produce the recombinant virus stock. This virus stock can be used to transduce cells to introduce the polynucleotide into the genome of the target cells.

The recombinant virus whose genome lacks all genes required to make viral proteins can transduce only once and cannot propagate. These viral vectors which are only capable of a single round of transduction of target cells are known as replication defective vectors. Hence, the polynucleotide is introduced into the host/target cell genome without the generation of potentially harmful retrovirus. A summary of the available packaging lines is presented in Coffin et al., 1997 (ibid).

Retroviral packaging cell lines in which the gag, pol and env viral coding regions are carried on separate expression plasmids that are independently transfected into a packaging cell line are preferably used. This strategy, sometimes referred to as the three plasmid transfection method (Soneoka et al., 1995), reduces the potential for production of a replication-competent virus since three recombinant events are required for wild type viral production. As recombination is greatly facilitated by homology, reducing or eliminating homology between the genomes of the vector and the helper can also be used to reduce the problem of replication-competent helper virus production.

An alternative to stably transfected packaging cell lines is to use transient transfected cell lines. Transient transfections may advantageously be used to measure levels of vector production when vectors are being developed. In this regard, transient transfection avoids the longer time required to generate stable vector-producing cell lines and may also be used if the vector or retroviral packaging components are toxic to cells. Components typically used to generate retroviral vectors include a plasmid encoding the gag/pol proteins, a plasmid encoding the env protein and a plasmid containing the polynucleotide. Vector production involves transient transfection of one or more of these components into cells containing the other required components.

One approach to control expression of the polypeptide of the present invention is to use the retroviral 5' LTR. The polynucleotide sequence may also be operably linked to an internal heterologous promoter. This arrangement permits flexibility in promoter selection.

The lentivirus group can be split into "primate" and "non-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV). Preferably the retroviral vector of the present invention is derivable from HIV.

A distinction between the lentivirus family and other types of retroviruses is that lentiviruses have the capability to infect both dividing and non-dividing cells. In contrast, other retroviruses—such as MLV—are unable to infect non-dividing cells such as those that make up, for example, muscle, brain, lung and liver tissue.

Even if the infection of non-dividing cells is a peculiar feature of lentivirus vectors, specific conditions may be provided for a both stable and efficient transduction. These include the expression of HIV-1 Vpr (Subbramanian et al., 1998; Vodicka et al., 1998), the presence of sequences from the HIV-1 pol polypurine tract (PPT) (Follenzi et al., 2000), and the activation state of monocyte/macrophages cultures (Re and Luban, 1997).

A significant reduction in the constitutive expression of vectors may be achieved by desensitizing them to the TNFα stimulation, for instance by deleting/mutating the TNFα responsive sequences (i.e. NF-kB binding sites) in the vector HIV-1 LTR promoter.

A more direct dependence on HIV-1 expression may also be accomplished by designing a vector whose transcripts undergo nuclear retention and degradation in the absence of the Rev/RRE interaction (Emerman et al., 1989; Malim et al., 1989). Furthermore, as already described for retrovirus vectors (Grignani et al., 1998), the use of a new generation of lentivirus vectors able to express the transgene without integrating the host genome could be of a valuable importance from a biosafety point of view.

The Tat protein regulates the levels of lentiviral gene expression. Due to the weak basal transcriptional activity of the long terminal repeat (LTR), expression of the provirus initially results in small amounts of multiply spliced transcripts coding for the Tat, Rev, and Nef proteins. Tat increases dramatically transcription by binding to a stem-loop structure (transactivation response element [TAR]) in the nascent RNA, thereby recruiting a cyclin-kinase complex that stimulates transcriptional elongation by the polymerase II complex. Preferably, the polynucleotide encoding mutant Vif is under the control of the HIV-1 LTR, which is activated by Tat and is therefore expressed only when the cells are infected by HIV-1. This vector design therefore allows minimizing expression of Vif in non-infected cells, thereby reducing immunogenicity, and induced at very high levels only when cells are infected by HIV-1. This confers a better protection with respect to other vector systems.

In one embodiment, the lentiviral vector of the present invention includes a selectable marker. Preferably, the selectable marker is truncated low affinity nerve growth factor receptor (ΔLNGFR). The common neutrophin receptor, low affinity Nerve Growth Factor Receptor gene (LNGFR) (also referred to as p75NTR) is not expressed on the majority of human hematopoietic cells, thus allowing quantitative analysis of transduced gene expression by immunofluorescence, with single cell resolution. Fluorescence activated cell sorter analysis of expression of LNGFR may be performed in transduced cells to study gene expression. Thus LNGFR may be utilised in the present invention as a selection marker. Further details on analysis using LNGFR may be found in Mavilio 1994. A truncated LNGFR, ΔLNGFR, is described in Mavilio 1994.

The selectable marker may be operably linked to an internal promoter or expressed from the 5'LTR.

The lentiviral vector of the present invention may be delivered by cells such as monocytes, macrophages, lymphocytes or hematopoietic stem cells. In particular a cell-dependent delivery system is used. In this system the lentiviral vector is introduced into one or more cells ex vivo and the cell(s) are then introduced into the patient.

The lentiviral vectors of the present invention may be administered alone but will generally be administered as a pharmaceutical composition.

Treatment

The present invention relates to the treatment of HIV infection or related conditions. It is to be appreciated that all references herein to treatment include curative, palliative and prophylactic treatment of HIV related diseases. The treatment of mammals is particularly preferred. Both human and veterinary treatments are within the scope of the present invention.

Thus, the present invention can be used to effect intracellular immunisation so as to prevent, or at least substantially inhibit, initial HIV infection in an individual at risk from such an infection. It can also be used in the therapeutic treatment of an HIV positive patient by blocking, or at least slowing the spread of the infection, and preventing or at least delaying the onset of AIDS or ARC.

In a preferred embodiment of the present invention, there is provided a method for imparting resistance to HIV infection or superinfection comprising removing an HIV-permissible cell from a patient, transducing the cell with the lentiviral vector of the present invention so as to achieve integration the HIV mutant Vif and reintroducing the cell into a patient. Such ex vivo methods are described in Ferrari et al., (1991). Alternatively the retroviral vector may be delivered to a cell in vivo.

Integration of the lentiviral vector into nuclear genomes of cells can be monitored using, e.g. PCR in conjunction with sequencing or Southern hybridisations.

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences, Mack Publishing Co. (A. R. Gennaro edit. 1985).

The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Polynucleotides/vectors encoding polypeptide components for use in affecting viral infections may be administered directly as a naked nucleic acid construct, preferably further comprising flanking sequences homologous to the host cell genome. When the polynucleotides/vectors are administered as a naked nucleic acid, the amount of nucleic acid administered may typically be in the range of from 1 μg to 10 mg, preferably from 100 μg to 1 mg.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

The composition of the present invention may also be used in conjunction with other antiretroviral drugs, in particular anti-HIV treatments such as AZT and ddI.

The routes of administration and dosages described are intended only as a guide since a skilled practitioner will be able to determine readily the optimum route of administration and dosage for any particular patient and condition.

Further preferred features and embodiments of the present invention will now be described by way of non-limiting examples.

Example 1

Materials and Methods

Cells

CEM A3.01 is a derivative clone of the T-lymphoblastoid CEM cell line, highly susceptible to HIV-1 cytopathic effect (Folks et al., 1985). The CEM A3.01, CEMss (Nara et al., 1988), Sup-T1 (Smith et al., 1984) and PM1 cells (Lusso et al., 1995) were grown in RPMI 1640 supplemented with 10% FCS (EuroClone Ltd, UK) and a combination of penicillin streptomycin and glutamine (PSG). The human kidney 293T cells were propagated in Iscove's Modified Dulbecco's Medium (IMDM) supplemented with 10% FCS and PSG.

Human neonatal leukocytes were purified from umbilical cord blood by centrifugation on a Ficoll-Hypaque gradient (Lymphoprep, Nycomed Pharma AS, Norway). CD4+ T cells were isolated by negative selection using CD4+ T cell isolation kit II (Miltenyi Biotec, Sunnyvale, Calif., USA). Purity (>95%) and the naïve phenotype were confirmed by flow cytometry using the anti-CD4, anti-CD45RA and anti-CD45RO Abs, respectively (BD Pharmingen™). CD4+ T lymphocytes were cultured for 3 days in X-VIVO-15 (Bio-Whittaker, Cambrex Bio Science, Verviers, Belgium) containing 10% human serum, 50 U/ml IL-2 (Chiron, Emeryville, Calif.), 25 U/ml of IL-7 (ImmunoTools, Germany) and in the presence of Dynabeads CD3/CD28 T cell expander (Dynal Lake Success, N.Y., USA) at the ratio of 0.5 beads/cell.

Plasmids

The lentiviral vector PΔN was generated by cloning the PGK-ΔLNGFR cassette, (Bonini et al., 1997) encoding a truncated form of the low affinity nerve growth factor receptor (ΔLNGFR) under the control of the phosphoglycerokinase (PGK) promoter, in the ClaI/SacII sites of the lentiviral vector pHR2 (Dull et al., 1998). The F12-VifPΔN and Vif-PΔN vectors were obtained by inserting a PCR-amplified, 611-bp F12-vif or wild-type (WT) vif sequence respectively in the ClaI site of the PΔN vector. The WT HIV-$1_{NL4-3}$ (acc. # M19921), and the F12-HIV-1 (acc. # Z11530) DNAs were used as vif PCR templates using the following primers:

for: 5'-GCAAAGAATCGATGGGATTATGGAAAACAG-3';

rev. 5'-CTCCTCTAATCGATGCTAGTGTCCATTCATTG-3' (ClaI sequence in bold). All PCR-amplified fragments and cloning junctions were fully sequenced.

We generated, starting from the previously described PΔN lentiviral vector (Vallanti et al, 2005), three vectors Chim1PΔN, Chim2PΔN and Chim3PΔN carrying chimeric WT/F12 vif genes. Chim1PΔN encodes the first N-terminal 87 amino acids of F12-vif and the remaining 106 amino acids of WT-vif Chim2PΔN encodes a chimeric protein in which the two domains have been swapped with respect to Chim1PΔN, and finally Chim3PΔN encodes a chimeric protein in which the amino acid region 126-170 of F12-Vif has been inserted in a WT-Vif backbone. The first two chimeric genes were obtained using as PCR template the genome of two NL4-3 HIV-1 molecular clone mutants in which the BSpMI-PflMI (259 bp) and the PflMI-EcoRI (440 bp) fragments from the F12-HIV genome were replaced, respectively. The third vector was generated by DNA synthesis by Primm s.r.l (Milano, Italy). The three chimeric genes were cloned into the ClaI site in the PΔN empty vector. All PCR-amplified fragments and cloning junctions were checked by sequencing. The F12-VifPΔN and the WT-VifPΔN were previously described. The pCEM15:HA (Sheehy et al., 2002) plasmid was a gift from M. Malim (King's College, London, UK).

Production of Pseudo-Typed Lentiviral Vectors

Pseudo-typed lentiviral vector stocks were produced by transient co-transfection of 293T cells with the transfer vector, a 2nd generation minimal packaging construct pCMVΔR8.74, expressing Gag, Pol, Tat and Rev, and the pMD.G plasmid encoding the vesicular stomatitis envelope glycoprotein, VSV-G (Zufferey et al., 1997). Cells were seeded at $0.4\times10^6$/ml 24 hours before transfection with the three plasmids at the 2:1:3 ratio by Fugene™6 (Roche Diagnostics Corporation, Indianapolis, Ind.). Supernatants were harvested 48-72 hours after transfection, cleared by low speed centrifugation (10 min at 1,500 rpm), and filtered through a 0.45-μm pore-size filter. Viral titers were calculated by transduction of cells with serial dilution of the viral stocks. Virus stock normalisation was achieved using standardised RT assay and p24 Ag ELISA procedures (Coulter Corporation, Westbrook, Me.).

Transduction and ΔLNGFR Immune Selection of Cells.

Cells were transduced by spinoculation. Briefly, RT assay-normalised supernatants of each VSV-G pseudo-typed vector were incubated with $1\times10^6$ cells in a final volume of 2 ml (MOI from 0.5 to 5), and centrifuged at 2,200 rpm for 1 hour in the presence of polybrene (8 μg/ml). After 48 hours, cells were washed with PBS and fresh complete medium was added. Transduction efficiency was monitored at least one week after spinoculation by flow cytometry analysis of ΔLNGFR expression (FACScan, Becton Dickinson, Mountain View, Calif.) using the anti-human p75-LNGFR monoclonal antibody 20.4 (ATCC, Rockville, Md.) and R-phycoerythrin (RPE)-conjugated goat anti-mouse serum (Southern Biotechnology Associates, Birmingham, Ala.). Immune selection of $\Delta LNGFR^+$ cells was obtained by magnetic cell sorting using MiniMACS microbeads (Miltenyi Biotec Inc., Sunnyvale, Calif.) according to the manufacturer's instructions. ΔLNGFR cell purity was >92% by FACS staining. Primary T cells were transduced by a modified spinoculation protocol (polybrene concentration: 4 μg/ml; viral supernatant replaced with fresh medium after overnight incubation). $\Delta LNGFR^+$ T-lymphocytes were selected 3 days after spinoculation as described for cell lines.

Western Blot Analysis

Whole-cell protein extracts (40 μg) were prepared as previously described (Bovolenta et al., 2002), size-fractionated by 12.5% SDS-PAGE, and transferred to Hybond ECL nitrocellulose membranes (Amersham, Little Chalfont, UK) by electro-blotting. Membranes were blocked in 5% low-fat dry milk for 1 hour at room temperature, and then incubated overnight at 4° C. with the appropriate primary Ab. HIV-$1_{HXB2}$ Vif rabbit antiserum (Goncalves et al., 1994) was obtained from Dana Gabuzda through the AIDS Research and Reference Reagent Program (Division of AIDS, NIAID, NIH, Bethesda, Md.), and used at 1:1,000 dilution. The rabbit polyclonal Ab against human actin (Sigma Chemical Corp., St. Louis, Mo.), was used at 1:250 dilution. A serum obtained from an AIDS patient, recognising all the major HIV-1 proteins, was used at 1:2,000 dilution. Ab binding was visualised by horseradish peroxidase-conjugated secondary Ab, anti-rabbit and anti-human Abs at a dilution of 1:10,000 (Amersham, Little Chalfont, UK) by an enhanced chemiluminescence system (ECL, Amersham).

Northern Blot Analysis

Figure 14:
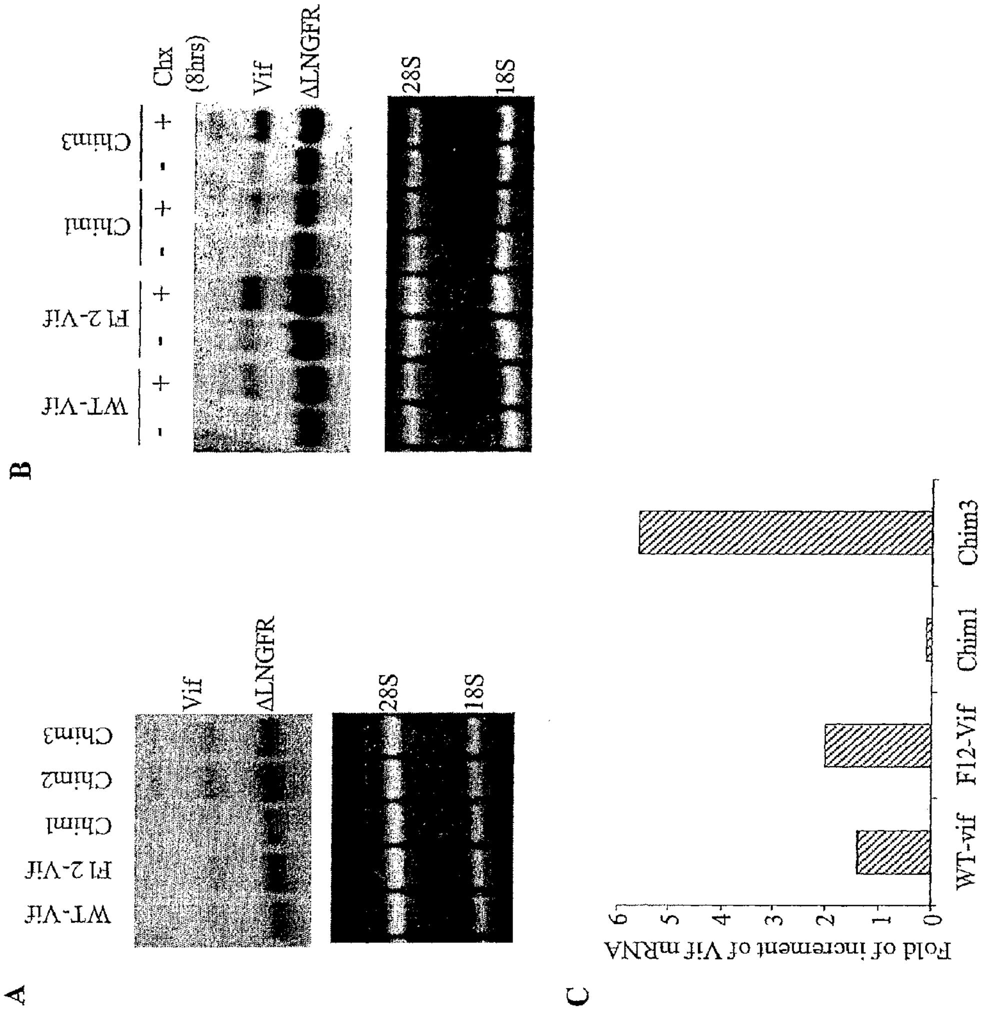
FIG. 14 shows the accumulation of Chim3 mRNA after cycloheximide treatment in non permissive cells. A. Total RNA (10 μg) was extracted from non permissive CEM A3.01 cells and fractionated RNA was then hybridized with the NGFR probe. B. Total RNA was extracted from non permissive CEM A3.01 cells either treated or not with cycloheximide (10 μg/ml) for 8 hours and fractionated RNA was then hybridized with the NGFR probe. C. Fold of increment of Vif mRNA was calculated by Phosphorimager quantification of the relative bands normalized on the NGFR bands.

CEM A3.01 cells were left untreated or treated with cycloheximide (10 μg/ml; Calbiochem®) for 8 hours. Total RNA was extracted by Trizol Reagent (Life Technologies™ Inc., Gaithersburg, Md.) according to manufacturer's instructions, run on 0.8% agarose-formaldehyde gels, transferred onto Hybond-N membrane (Hybond-N, Amersham) by capillary transfer, probed with 106 dpm/ml of a $^{32}P$-labelled 1-kb ΔLNGFR fragment in PerfectHyb PLUS hybridization buffer (Sigma Chemical Corp., St. Louis, Mo.), and exposed to X-ray films at −70° C. (FIG. 14).

HIV-1 Infection

Cells were acutely infected with the following HIV-1 strains: the laboratory adapted X4 HIV-1 IIIB/LAI (ABI, Advanced Biotechnologies, Columbia, Md.), the molecular clones X4 HIV-$1_{NL4-3}$ and its Δvif derivative (Gibbs, 1994), the molecular clones R5 HIV-1 AD8 (ABI, Advanced Biotechnologies, Columbia, Md.) and the pAD1vif1 HIV kindly donated by K. Peden (FDA, NIH, Bethesda, Md.). Viruses (MOI ranging from 0.01 to 1) were adsorbed to the cells for 2-5 hours at 37° C., then washed out twice with PBS. Cells were eventually resuspended in complete medium and seeded at $0.5\text{-}1\times10^6$/ml in triplicate in 96-well plate. Culture supernatants were harvested every 4 days and stored at −80° C. until tested for $Mg^{2+}$-dependent RT-activity assay or p24 ELISA following standard procedures.

Example 2

Tat Dependent Expression of Mutant Vif

We have shown that the chimeric proteins are expressed in a Tat-dependent manner in 293T cells co-transfected with the lentiviral vectors encoding the Vif mutants and the packaging construct (as a source of Tat) (FIG. 7).

Whole-cell extracts (WCE) were prepared as previously described {Bovolenta, 2002 #205}. Proteins were size-fractionated by SDS-PAGE, and transferred to Hybond ECL nitrocellulose membranes (Amersham, Little Chalfont, UK) by electroblotting. Membranes were blocked in 5% low-fat dry milk, and then incubated with the appropriate primary Ab. HIV-$1_{HXB32}$ Vif rabbit antiserum {Goncalves, 1994 #241} was obtained from Dana Gabuzda through the AIDS Research and Reference Reagent Program (Division of AIDS, NIAID, NIH, Bethesda, Md.), and used at 1:1,000 dilution.

The proteins have different intracellular stability, in that F12-Vif (FIG. 2), Chim2 (FIGS. 4A,B) and Chim3 (FIGS. 5A,B) are no longer present, whereas WT-Vif (FIG. 1C) and Chim1 (FIGS. 3A,B) are still accumulated at 72 hours (FIG. 7).

Example 3

Mutant Vif Constructs Inhibits Replication of HIV-1 in T Cells

Figure 8:
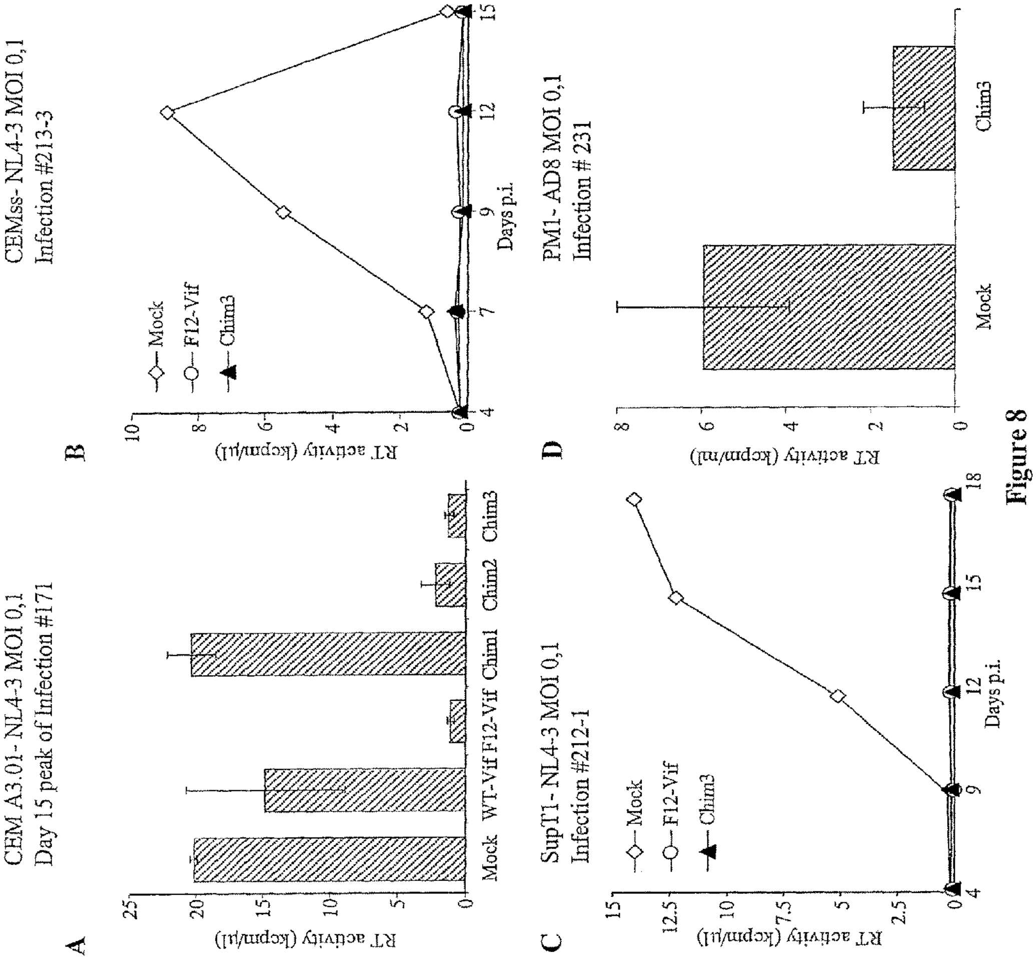
FIG. 8 shows the antiviral activity of the chimeric proteins in T cell lines. A. NP CEM A3.01 mock-transduced (Mock) and F12-Vif- and Chim3PΔN-transduced cells were infected with the X4 molecular clone HIV-1 NL4-3 at the MOI of 0.1. The mean of triplicate values measured at the peak of a kinetic of infection (day 15) by RT assay are shown. B. Kinetic of infection of permissive mock-transduced and LV-transduced CEMss cells infected with the X4 HIV-1 NL4-3 at the MOI of 0.1. C. Permissive SupT-1 mock-transduced and LV-transduced cells infected with the X4 HIV-1 NL4-3 at the MOI of 0.1. D. Non permissive mock-transduced and Chim3PΔN-transduced PM1 cells were infected with the R5 HIV-1 AD8 at the MOI of 0.1 and RT activity measured at 6 days post infection.

We initially compared the potential anti-viral activity of the three chimera with that of F12-Vif by infecting mock-transduced and LV-transduced CEMA3.01 cells with the X4 molecular clone NL4-3 at the MOI of 0.1. FIG. 8A shows that Chim1, which comprises the N-terminal region of F12-Vif, has no antiviral activity, whereas both Chim2 and Chim3 (expressing C-terminal domains of F12-Vif) inhibit HIV-1 replication in a manner comparable to that of F12-Vif. Although the sequence of F12-Vif is shorter in Chim3 than in Chim2 (45 aa vs 104 aa comprising 6 vs 9 unique aa substitutions, respectively) its anti-viral activity is slightly higher than that of Chim2. Therefore, from hereon we report only the effect of Chim3 in comparison to that of F12-Vif, omitting for simplicity that of Chim2 always paralleling that of Chim3. We verified the HIV inhibitory activity of Chim3 in the CEMss (FIG. 8B) and Sup-T1 (FIG. 8C) permissive cells by infecting them with X4 NL4-3 HIV-1 at the MOI of 0.1. In both cases Chim3 inhibits HIV-1 replication as efficiently as F12-Vif. Finally, to test the inhibitory activity of Chim3 against an R5 HIV-1 strain, we used the PM1 cells as the only T cell line that can be infected with an R5 HIV-1 strain (Lusso et al., 1995). Mock-transduced and Chim3PΔN-transduced cells were challenged with the HIV-1 AD8 molecular clone at the MOI of 0.1, and analyzed for viral production at day 6 post infection. As shown in FIG. 8D, cells expressing Chim3 show a four-fold less viral release over mock-transduced cells.

Example 4

Figure 9:
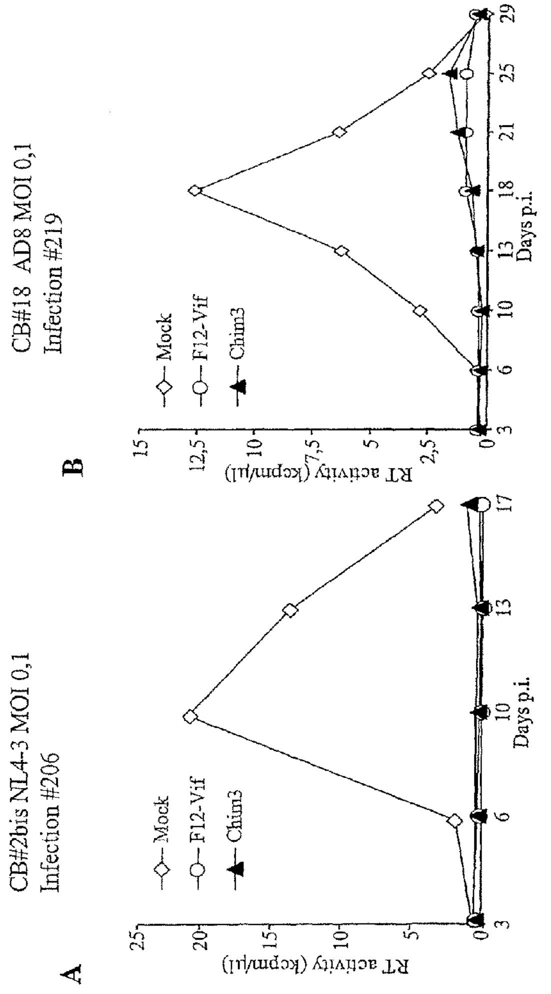
FIG. 9 shows the antiviral activity of Chim3 in CD4+ T lymphocytes. Cord blood derived CD4+ T lymphocytes mock transduced and LVs-transduced were infected with either the X4 HIV-1 NL4-3 (A) or R5 molecular clone HIV-1 AD8 at the MOI of 0.1 (B).

Chim3 Inhibits the Replication of Both X4 and R5 HIV-1 Strains in Cord Blood Derived CD4+ T Lymphocytes Pre-activated CD4+ T lymphocytes derived from cord blood of healthy normal donors were transduced with the different LVs, and infected with the X4 HIV-1 NL4-3 strain at the MOI of 0.1. In contrast to mock-transduced cells, T lymphocytes carrying the integrated Chim3 gene control HIV-1 infection throughout the experiment as well as F12-Vif (FIG. 9A). Similar results were obtained with CD4+ T lymphocytes derived from a different donor and infected with the R5 molecular clone HIV-1 ADS at the MOI of 0.1 (FIG. 9B).

Example 5

Figure 10:
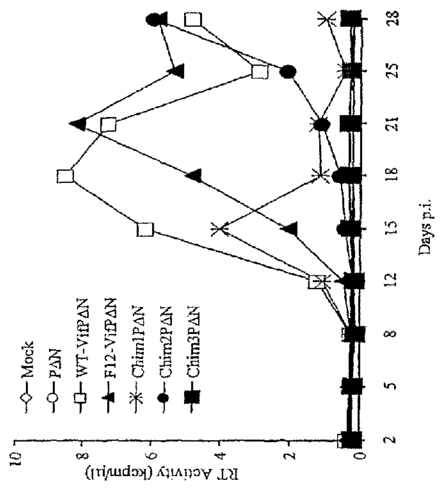
FIG. 10 shows the kinetics of HIV-1 replication in CEM A3.01 cells transduced with the indicated lentiviral vectors and then infected with HIV-$1_{NL4-3}$ at the MOI of 0.1.

Chim3 Does Not Rescue the Replication of Δvif HIV-1 in CB-Derived CD4+ T Lymphocytes To investigate whether the F12-Vif, Chim2 and Chim3 inhibitory activity was dependent on the presence of WT-Vif, we infected the non-permissive CEM A3.01 mock- and vector-transduced cells with Δvif HIV-1 at the MOI of 0.1 (FIG. 10). As expected, Δvif HIV-1 does not replicate in mock- and PΔN-transduced cells, while it efficiently grows in cells in which WT-Vif is supplied in trans. Remarkably, Δvif HIV-1 is released also from F12-Vif- and Chim2-, but not from Chim3-expressing cells, indicating that the Chim3 Vif is safer than Chim2 in case it encounters Δvif HIV-1 quasispecies silently harboured in a patient (FIG. 10).

Figure 11:
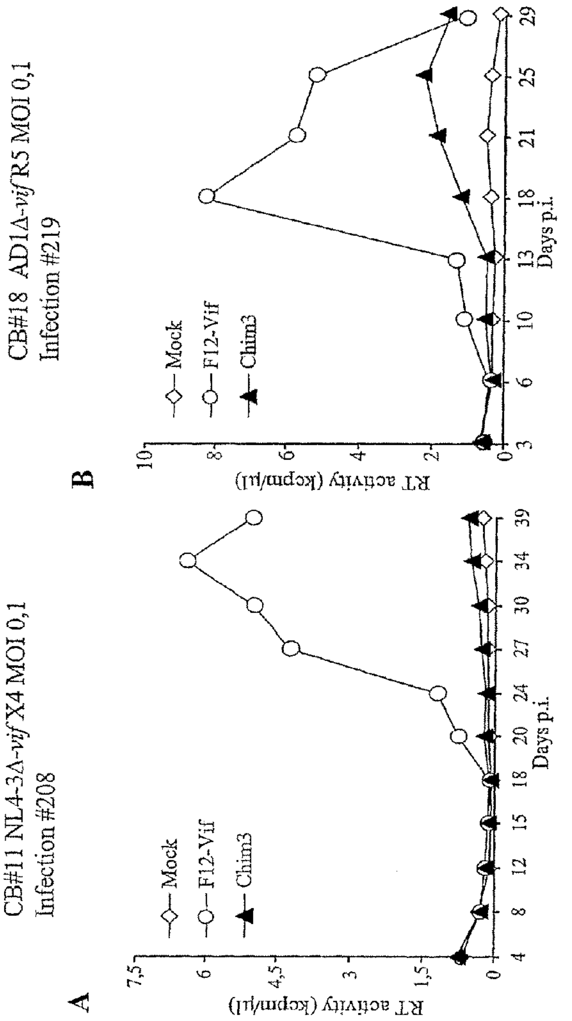
FIG. 11 shows that Chim3 does not rescue the replication of X4 and R5 Δvif HIV-1 in CD4+ T lymphocytes. CD4+ T lymphocytes mock-transduced or LVs-transduced were infected with the X4 Δvif-HIV (A) and R5 HIV-1 AD-1vif (B) molecular clones at the MOI of 0.1. HIV-1 growth was followed for 39 and 29 days, respectively.

In a further experiment we infected CD4+ T lymphocytes mock-transduced, F12-Vif- and Chim3-transduced cells with vif-deficient virus generated either in the context of X4 or R5 tropism at the MOI of 0.1 and followed the kinetic of infection for 39 days (X4 Δvif HIV, FIG. 11A) and 29 days (R5 Δvif HIV, FIG. 11B), respectively. In contrast to what we have previously described (22) and here confirmed on F12-Vif, Chim3 does not rescue the replication of both vif-deficient viruses although a weak level of viral replication is observed with the R5-tropic strain (FIG. 11B). Altogether these results suggest that Chim3 not only inhibits HIV replication at level similar to that reached by F12-Vif, but more importantly, does not salvage the replication of vif-deficient viruses. This therefore makes Chim3 a better candidate for an anti-HIV gene therapy approach compared to F12-Vif. Chim3 shows in fact a truly dominant negative phenotype in regard to the effect of Vif as counteracting factor of the HIV-1 restriction factor hHA3G.

Example 6

Figure 12:
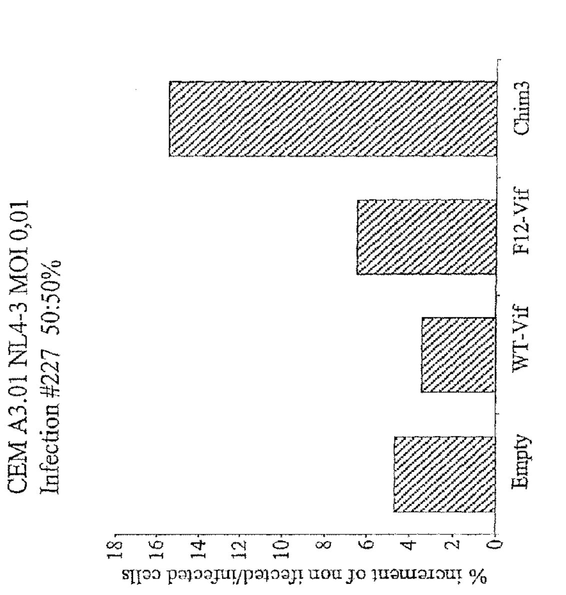
FIG. 12 shows the selective advantage of F12-Vif- and Chim3-transduced over mock-transduced cells after HIV-1 infection. CEM A3.01 cells LVs-transduced and mock-transduced were mixed and cultivated at the ratio of 50:50 and then infected with the X4 HIV-1 NL4-3 at the MOI of 0.01. The percentage of increment of transduced cells (NGFR+ cells) was calculated at day 20 p.i. between infected and non infected cells.

Chim3 Confers Survival Advantage to Transduced Compared to Mock Transduced HIV-1 Infected Cells To investigate whether Chim3-transduced cells could show selective advantage compared to the mock transduced counterparts, we mixed CEMA3.01 LVs-transduced with mock-transduced cells in equal proportion (50:50). Cells were then splitted in two populations, one left uninfected and the other one infected with X4 HIV-1 NL4-3 at the MOI of 0.01. Percentage of increment of NGFR+ infected over non infected cells was calculated at day 20 of culture. Expression of NGFR was monitored by FACS analysis. FIG. 12 shows that in all cell types there is an increment of NGFR+ cells after HIV-1 infection. However, the enhancement of Chim3- and F12-Vif-transduced cells is from 2 to 5 higher compared to the control cells, indicating that both therapeutic genes confers a stronger selective advantage to the genetically modified cells.

Example 7

Chim3 is Preferentially Degraded in the Proteasome Only in Non Permissive Cells and Its Level Inversely Correlates with that of Cellular Factor Human APOBEC3G (hA3G)

Based on the fact that Chim3, in contrast to F12-Vif, behaves like a truly dominant negative factor, we wondered what is the level of hA3G in Chim3 transduced cells. We initially analyzed the basal level of expression of the chimera in uninfected transduced non permissive CEM A3.01 and permissive Sup-T1 cells. Strikingly, Chim2 and Chim3 expression is much lower than that of the other Vifs (FIG. 13A) suggesting a different stability or expression of the two chimera.

Figure 13:
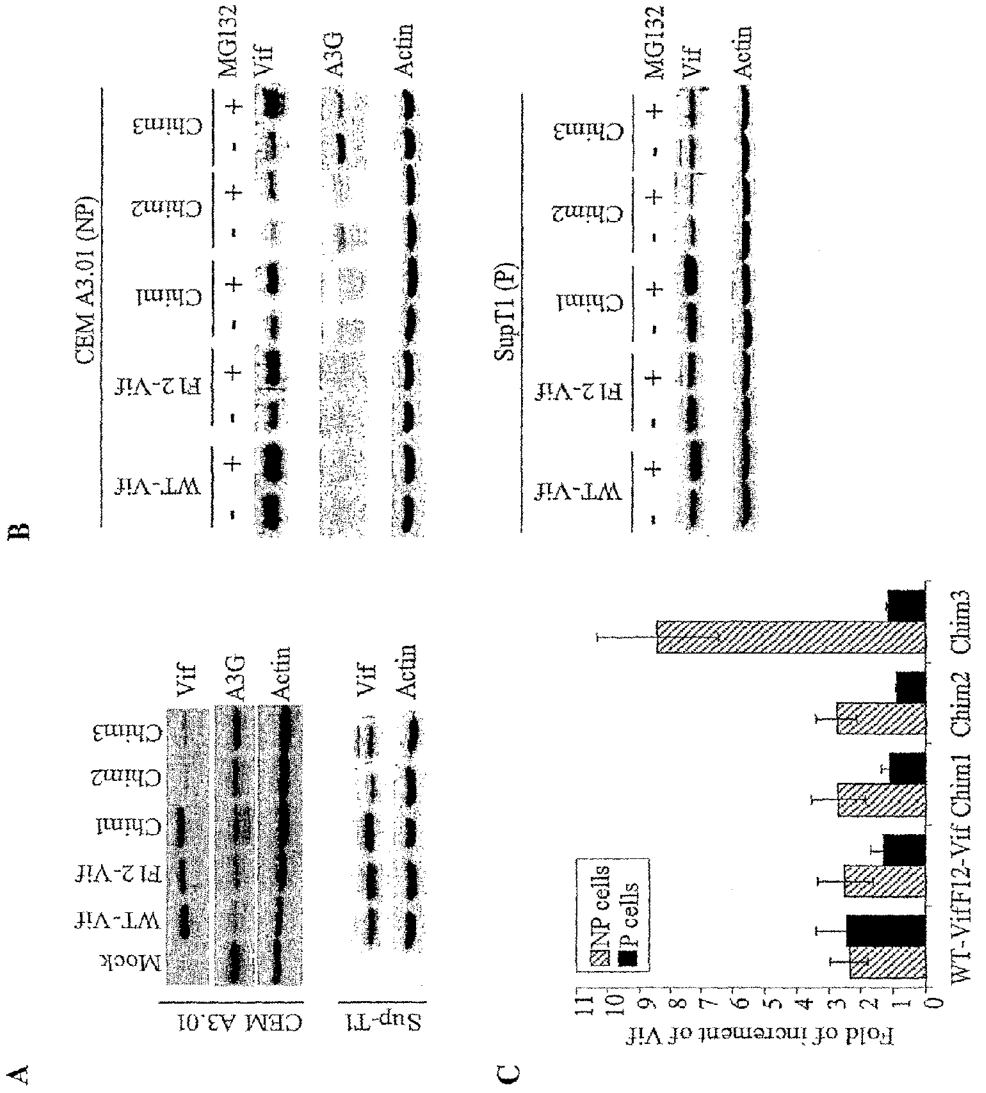
FIG. 13 shows the lower expression of Chim2 and Chim3 compared to WT-Vif and that Chim3 is degraded by proteasome more efficiently in non permissive than in permissive cells. A. Western blot analysis of the basal level of Vif and hA3G proteins in mock and LV-transduced either non permissive CEM A3.01 or permissive SupT-1 cells. B. Western blot analysis of whole cell extracts derived from either uninfected permissive (SupT-1) or non permissive (CEM A3.01) cells treated for 18 hours with the proteasome inhibitor MG132. Filters were probed sequentially with the anti-Vif, anti-hA3G (only in non permissive cells) and anti-actin Abs. C. Fold of increment of Vif proteins were calculated by measuring the intensity of the bands with or without MG132 treatment and normalising for equal amount of protein with the actin bands. Quantifications have been done on three independent experiments.

As Vif is degraded in non permissive HeLa and 293T cells by the proteasome (Fujita et al., 2004), we next interrogated the level of Vif proteins in permissive and non permissive cells in the presence or absence of the proteasome inhibitor MG132. As shown in the upper panel of FIG. 13B, the expression of both Chim2 and Chim3 is lower than the other Vifs also in Sup-T1 cells and the treatment with MG132 induces only weak accumulation of the proteins (FIG. 13C). In contrast, Chim3 accumulates after MG132 treatment about 3 times more than the other Vifs (FIG. 13B, lower panel and 13C). More importantly, hA3G is detectable in western blot analysis only in Chim3 expressing cells and its level inversely correlates with that of Chim3 in MG132 treated cells (FIG. 13B, middle panel). These results indicate that Chim3 is preferentially degraded in the proteasome only in non permissive cells and its low level allows the normal expression of hA3G.

Example 8

Chim3 is Normally Expressed by the Vector and its mRNA Accumulates After Cycloheximide Treatment To determine whether the low expression of Chim3 depends also by low transcription, we performed Northern blot analysis of total RNA obtained from LV-transduced uninfected CEM A3.01 cells using the NGFR probe. The LVs transcribe three different RNA species, the full length and the spliced RNAs, which are driven by the 5'LTR of the vector, and the constitutive PGK-ΔLNGFR mRNA (Vallenti et al., 2005). In uninfected cells, which lack Tat and Rev, the 5'LTR indeed functions—the Vif proteins accumulate—but weaker than in infected cells. Therefore, the only two bands detected correspond to the spliced RNA containing Vif and the constitutive ΔLNGFR one. Surprisingly, the expression of Chim2 and Chim3 LVs is stronger than the other LVs (FIG. 14A) and inversely correlates with the level of protein synthesized. To further investigate the reason of this apparent discrepancy, we treated the cells for 8 h with cycloheximide that blocks the protein synthesis. Of note, the accumulation of Chim3 mRNA is higher than the others Vifs (FIGS. 14B and C). These results suggest that the analyzed Vifs, but not Chim3, regulate their own transcription by a negative feed-back mechanism. Chim3 is normally transcribed and its mRNA is poorly transcribed likely because the protein is readily degraded by the proteasome.

Example 9

Immunogenicity

By itself, Vif is one of the less immunogenic among the HIV-1 proteins (Addo et al., 2003). The mutant Vif polypeptides of the present invention are not expected to differ significantly from WT-Vif under this respect, at least on the basis of both BIMAS (http://bimas.cit.nih.gov/) and RANKPEP (http://www.mifoundation.org/Tools/rankpep.html) algorithms for predicting HLA-I binding peptides (data not shown). Low immunogenicity and Tat-dependent expression of mutant Vif should avoid or at least minimize an immune response against uninfected retroviral-transduced cells in vivo. On the other hand, the wild-type HIV-1 LTR guarantees very high expression levels of the transgene in HIV-1 infected cells, a crucial requirement for the activity of a trans-dominant mutant protein.

REFERENCES

Richman Nature 2001; 410:995-1001.
Ho et al. Cell 2002; 110:135-138
Blankson et al. Annu. Rev. Med. 2002; 53:557-593
Buchschacher et al. Hum. Gene Ther. 2001; 12:1013-1019.
Woffendin et al. Proc. Natl. Acad. Sci. USA. 1996; 93:2889-2894
Ranga et al. Proc. Natl. Acad. Sci. USA. 1998; 95:1201-1206
Wong-Staal et al. Hum. Gene Ther. 1998; 9:2407-2425
Jacque et al. Nature. 2002; 418:435-438
Novina et al. Nat. Med. 2002; 8:681-686
Lee et al. Nat Biotechnol. 2002; 20:500-505
Coburn et al. J. Virol. 2002; 76:9225-9231
Qin et al. Proc. Natl. Acad. Sci. USA. 2003; 100:183-188
Baum et al. Blood 2003; 101:2099-2114.
Cullen et al. Cell 1998; 93:685-692
Frankel et al. Annu. Rev. Biochem. 1998; 67:1-25
Fisher et al. Science 1987; 237:888-893
Fouchier et al. J. Virol. 1996; 70:8263-8269
Gabuzda et al. J. Virol. 1992; 66:6489-6495
Sheehy et al. J. Virol. 1996; 70:1505-1511
Desrosiers et al. J. Virol. 1998; 72:1431-1437
Simon et al. J. Virol. 1996; 70:5297-5305
von Schwedler et al. J. Virol. 1993; 67:4945-4955
Sova et al. J. Virol. 1995; 69:2557-2564
Wieland et al. Virology. 1994; 203:43-51
Wieland et al. J. Gen. Virol. 1997; 78:393-400
Teng et al. Science 1993; 260, 1816-1819
Sova et al. J. Virol. 2001; 75:5504-5517
Zimmerman et al. Nature 2002; 415:88-92
Zhang et al. J. Virol. 2000; 74:8252-8261
Dettenhofer et al. J. Virol. 2000; 74:8938-8945
Liu et al. J. Virol. 1995; 69:7630-7638
Kao et al. J. Virol. 2003; 77:1131-1140
Mariani et al. Cell 2003; 114(1):21-31.
Fouchier et al. J. Virol. 1996; 70:8263-8269
Gabuzda et al. J. Virol. 1992; 66:6489-6495
von Schwedler et al. J. Virol. 1993; 67:4945-4955
Borman et al. J. Virol. 1995; 69:2058-2067
Bouyac et al. J. Virol. 1997; 71:2473-2477
Hoglund et al. Virology 1994; 201:349-355
Federico et al. AIDS Res. Hum. Retroviruses 1989; 5:385-396.
D'Aloja et al. J. Virol. 1998; 72 (5): 4308
Taddeo et al. J. Virol. 1996; 70:8277-8284.
Yang et al. J. Biol. Chem. 2001; 276 (7) 4888-4893
Mavilio et al. Blood 1994; 83, 1988-1997
Subbramanian et al. J. Exp. Med. 1998; 187, 1103-1111
Vodicka et al. Genes Dev. 1998; 12, 175-185
Follenziet et al. Nat. Genet. 2000; 25, 217-222
Re et al. Prog. Cell Cycle Res. 1997; 3, 21-27
Emerman et al. Cell 1989; 57, 1155-1165.
Malim et al. Nature 1989; 338, 254-257.
Grignani et al. Cancer Res. 1998; 58, 14-19.
Soneoka et al. Nucl. Acids Res. 1995; 23: 628-633
Ferrari et al. Science 1991; 251:1363
Folks et al. Proc. Natl. Acad. Sci. USA. 1985; 82:4539-4543
Bonini et al. Science 1997; 276:1719 1724
Dull et al. J. Virol. 1998; 72:8463-8471
Zufferey et al. J. Virol. 1998; 72:9873-9880
Zufferey et al. Nat. Biotechnol. 1997; 15:871-875
Bovolenta et al. Blood 2002; 99:224-231.
Goncalves et al. J. Virol. 1994; 68:704-712
Vicenzi et al. J. Virol. 1999; 73:7515-7523
Gibbs et al. AIDS Res. Hum. Retroviruses 1994; 10:343-350
Folks et al. Science 1987; 238:800-802
Folkes et al. Proc. Natl. Acad. Sci. USA. 1989; 86:2365-2368
Lecossier et al. Science. 2003; 300:1112
Harris et al. Cell. 2003; 113:803-809
Addo et al. J. Virol. 2003; 77:2081-2092
Navarro et al., 2004; Curr Opin Immunol 16:477-82
Trono, 2004; EMBO Rep 5:679-80
Clouse et al., J. Immunol. 1989, 142: 431-8
Bonini et al., 2003, Nat. Med. 9:367-9
Lusso et al., 1995, J. Virol. 69:3712-20
Nara et al., 1988, Nature 332:469-70
Smith et al., 1984, Cancer Res. 44:4657-60
Sheehy et al., 2002, 418:646-50
Fujita et al., 2004, Microbes Infect 6:791-8
Vallanti et al., 2005, Mol. Ther. 12:697-706

The invention claimed is:

1. An isolated polynucleotide encoding a mutant Vif, wherein the polynucleotide comprises a nucleotide sequence encoding the amino acid sequence shown in SEQ ID NO: 11.

2. A vector comprising a polynucleotide as defined in claim 1.

3. A vector according to claim 2 wherein the vector is a retroviral or lentiviral vector.

4. A vector according to claim 3 wherein the lentiviral vector is derivable from HIV.

5. A vector according to claim 3 wherein said polynucleotide is operably linked to a viral LTR.

6. A vector according to claim 3 wherein expression of said polynucleotide is tat dependent.

7. A vector according to claim 3 lacking the tat gene.

8. A vector according to claim 3 wherein expression of said polypeptide is under HIV-1 inducible control.

9. A vector according to claim 3 lacking any one or more, or all, of the gag, pol and env genes.

10. A vector according to claim 2 further comprising a polynucleotide sequence encoding a selectable marker gene.

11. A vector according to claim 2 further comprising a polynucleotide sequence encoding at least part of the p75 low affinity nerve growth factor receptor (LNGFR).

12. A vector according to claim 2 in the form of an integrated provirus.

13. A pharmaceutical composition comprising the polynucleotide of claim 1, the vector of claim 2 and a pharmaceutically acceptable carrier, diluent or excipient.

* * * * *

SEQUENCE LISTING

```
<160> NUMBER OF SEQ ID NOS: 37

<210> SEQ ID NO 1
<211> LENGTH: 192
<212> TYPE: PRT
<213> ORGANISM: Human immunodeficiency virus

<400> SEQUENCE: 1
```

-continued

Met Glu Asn Arg Trp Gln Val Met Ile Val Trp Gln Val Asp Arg Met
1 5 10 15

Arg Ile Arg Thr Trp Lys Ser Leu Val Lys His His Met Tyr Val Ser
20 25 30

Gly Lys Ala Arg Gly Trp Phe Tyr Arg His His Tyr Glu Ser Pro His
35 40 45

Pro Arg Ile Ser Ser Glu Val His Ile Pro Leu Gly Asp Ala Arg Leu
50 55 60

Val Ile Thr Thr Tyr Trp Gly Leu His Thr Gly Glu Arg Asp Trp His
65 70 75 80

Leu Gly Gln Gly Val Ser Ile Glu Trp Arg Lys Lys Arg Tyr Ser Thr
85 90 95

Gln Val Asp Pro Glu Leu Ala Asp Gln Leu Ile His Leu His Tyr Phe
100 105 110

Asp Cys Phe Ser Glu Ser Ala Ile Arg Lys Ala Leu Leu Gly His Ile
115 120 125

Val Ser Pro Arg Cys Glu Tyr Gln Ala Gly His Asn Lys Val Gly Ser
130 135 140

Leu Gln Tyr Leu Ala Leu Ala Ala Leu Ile Thr Pro Lys Lys Ile Lys
145 150 155 160

Pro Pro Leu Pro Ser Val Thr Lys Leu Thr Glu Asp Arg Trp Asn Lys
165 170 175

Pro Gln Lys Thr Lys Gly His Arg Gly Ser His Thr Met Asn Gly His
180 185 190

<210> SEQ ID NO 2
<211> LENGTH: 192
<212> TYPE: PRT
<213> ORGANISM: Human immunodeficiency virus

<400> SEQUENCE: 2

Met Glu Asn Arg Trp Gln Val Met Ile Val Trp Gln Val Asp Arg Met
1 5 10 15

Arg Ile Arg Thr Trp Lys Ser Leu Val Lys His His Met Tyr Val Ser
20 25 30

Gly Lys Ala Arg Gly Trp Phe Tyr Arg His His Tyr Glu Ser Pro His
35 40 45

Pro Arg Ile Ser Ser Glu Val His Ile Pro Leu Gly Asp Ala Arg Leu
50 55 60

Val Ile Thr Thr Tyr Trp Gly Leu His Thr Gly Glu Arg Asp Trp His
65 70 75 80

Leu Gly Gln Gly Val Ser Ile Glu Trp Arg Lys Lys Arg Tyr Ser Thr
85 90 95

Gln Val Asp Pro Glu Leu Ala Asp Gln Leu Ile His Leu Tyr Tyr Phe
100 105 110

Asp Cys Phe Ser Asp Ser Ala Ile Arg Lys Ala Leu Leu Gly His Ile
115 120 125

Val Ser Pro Arg Cys Glu Tyr Gln Ala Gly His Asn Lys Val Gly Ser
130 135 140

Leu Gln Tyr Leu Ala Leu Ala Ala Leu Ile Thr Pro Lys Lys Ile Lys
145 150 155 160

Pro Pro Leu Pro Ser Val Thr Lys Leu Thr Glu Asp Arg Trp Asn Lys
165 170 175

Pro Gln Lys Thr Lys Gly His Arg Gly Ser His Thr Met Asn Gly His

-continued

```
            180                 185                 190


<210> SEQ ID NO 3
<211> LENGTH: 192
<212> TYPE: PRT
<213> ORGANISM: Human immunodeficiency virus

<400> SEQUENCE: 3

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro His
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu Tyr Tyr Phe
            100                 105                 110

Asp Cys Phe Ser Asp Ser Ala Ile Arg Lys Ala Leu Leu Gly His Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
            180                 185                 190


<210> SEQ ID NO 4
<211> LENGTH: 192
<212> TYPE: PRT
<213> ORGANISM: Human immunodeficiency virus

<400> SEQUENCE: 4

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Ile Ser
            20                  25                  30

Lys Lys Ala Lys Gly Trp Phe Tyr Arg His His Tyr Glu Ser Thr His
        35                  40                  45

Pro Arg Val Ser Ser Glu Val His Ile Pro Leu Gly Asp Ala Lys Leu
    50                  55                  60

Val Ile Thr Thr Tyr Trp Gly Leu His Thr Gly Glu Arg Glu Trp His
65                  70                  75                  80

Leu Gly Gln Gly Val Ala Ile Glu Trp Arg Lys Lys Lys Tyr Ser Thr
                85                  90                  95

Gln Val Asp Pro Gly Leu Ala Asp Gln Leu Ile His Leu His Tyr Phe
            100                 105                 110

Asp Cys Phe Ser Glu Ser Ala Ile Lys Asn Ala Ile Leu Gly Tyr Arg
        115                 120                 125

Val Ser Pro Arg Cys Glu Tyr Gln Ala Gly His Asn Lys Val Gly Ser
```

```
    130                 135                 140

Leu Gln Tyr Leu Ala Leu Ala Ala Leu Ile Thr Pro Lys Lys Thr Lys
145                 150                 155                 160

Pro Pro Leu Pro Ser Val Lys Lys Leu Thr Glu Asp Arg Trp Asn Lys
                165                 170                 175

Pro Gln Lys Thr Lys Gly His Arg Gly Ser His Thr Met Asn Gly His
            180                 185                 190


<210> SEQ ID NO 5
<211> LENGTH: 192
<212> TYPE: PRT
<213> ORGANISM: Human immunodeficiency virus

<400> SEQUENCE: 5

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro His
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu Tyr Tyr Phe
            100                 105                 110

Asp Cys Phe Ser Asp Ser Ala Ile Arg Lys Ala Leu Leu Gly His Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
            180                 185                 190


<210> SEQ ID NO 6
<211> LENGTH: 192
<212> TYPE: PRT
<213> ORGANISM: Human immunodeficiency virus

<400> SEQUENCE: 6

Met Glu Asn Arg Arg Gln Val Met Ile Val Trp Gln Ala Asp Arg Met
1               5                   10                  15

Arg Ile Arg Thr Trp Lys Ser Leu Val Lys His His Met Tyr Ile Ser
            20                  25                  30

Lys Lys Ala Lys Gly Arg Phe Tyr Arg His His Tyr Glu Ser Thr His
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
```

-continued

```
                85                  90                  95

Gln Val Asp Pro Asp Leu Ala Asp His Leu Ile His Leu His Tyr Phe
            100                 105                 110

Asp Cys Phe Ser Asp Ser Ala Ile Arg Lys Ala Ile Leu Gly His Arg
        115                 120                 125

Val Ser Pro Ile Cys Glu Phe Gln Ala Gly His Asn Lys Val Gly Pro
    130                 135                 140

Leu Gln Tyr Leu Ala Leu Thr Ala Leu Ile Thr Pro Lys Lys Ile Lys
145                 150                 155                 160

Pro Pro Leu Pro Ser Val Lys Lys Leu Thr Glu Asp Arg Trp Asn Lys
                165                 170                 175

Pro Gln Lys Thr Lys Gly His Arg Gly Ser His Thr Ile Asn Gly His
            180                 185                 190


<210> SEQ ID NO 7
<211> LENGTH: 192
<212> TYPE: PRT
<213> ORGANISM: Human immunodeficiency virus

<400> SEQUENCE: 7

Met Glu Asn Arg Trp Gln Val Met Ile Val Trp Gln Val Asp Arg Met
1               5                   10                  15

Arg Ile Arg Thr Trp Ile Ser Leu Val Lys His His Ile Tyr Ile Ser
            20                  25                  30

Lys Lys Ala Lys Gly Trp Phe Tyr Lys His His Tyr Glu Ser Thr Asn
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Gly Leu Ala Asp Gln Leu Ile His Arg Tyr Tyr Phe
            100                 105                 110

Asp Cys Phe Ser Glu Ser Ala Ile Arg Asn Ala Ile Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190


<210> SEQ ID NO 8
<211> LENGTH: 192
<212> TYPE: PRT
<213> ORGANISM: Human immunodeficiency virus

<400> SEQUENCE: 8

Met Glu Asn Arg Trp Gln Val Met Ile Val Trp Gln Val Asp Arg Met
1               5                   10                  15

Arg Ile Asn Thr Trp Lys Arg Leu Val Lys His His Met Tyr Ile Ser
            20                  25                  30

Arg Lys Ala Lys Asp Trp Phe Tyr Arg His His Tyr Glu Ser Thr Asn
```

```
        35                  40                  45

Pro Lys Ile Ser Ser Glu Val His Ile Pro Leu Gly Asp Ala Lys Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190


<210> SEQ ID NO 9
<211> LENGTH: 192
<212> TYPE: PRT
<213> ORGANISM: Artificial sequence
<220> FEATURE:
<223> OTHER INFORMATION: Chimeric protein Chim1PdeltaN encoding the
      first N-terminal 87 amino acids of F12-vif and the remaining
      106 amino acids of wild type-vif.

<400> SEQUENCE: 9

Met Glu Asn Arg Trp Gln Val Met Ile Val Trp Gln Val Asp Arg Met
1               5                   10                  15

Arg Ile Arg Thr Trp Ile Ser Leu Val Lys His His Ile Tyr Ile Ser
            20                  25                  30

Lys Lys Ala Lys Gly Trp Phe Tyr Lys His His Tyr Glu Ser Thr Asn
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190


<210> SEQ ID NO 10
```

```
<211> LENGTH: 192
<212> TYPE: PRT
<213> ORGANISM: Artificial sequence
<220> FEATURE:
<223> OTHER INFORMATION: Chimeric protein Chim2PdeltaN in which the
      F12-vif domain and the remaining 106 amino acids of Wild type-
      vif domain are swapped relative to Chim1PdeltaN.

<400> SEQUENCE: 10

Met Glu Asn Arg Trp Gln Val Met Ile Val Trp Gln Val Asp Arg Met
1               5                   10                  15

Arg Ile Asn Thr Trp Lys Arg Leu Val Lys His His Met Tyr Ile Ser
            20                  25                  30

Arg Lys Ala Lys Asp Trp Phe Tyr Arg His His Tyr Glu Ser Thr Asn
        35                  40                  45

Pro Lys Ile Ser Ser Glu Val His Ile Pro Leu Gly Asp Ala Lys Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Gly Leu Ala Asp Gln Leu Ile His Arg Tyr Tyr Phe
            100                 105                 110

Asp Cys Phe Ser Glu Ser Ala Ile Arg Asn Ala Ile Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190


<210> SEQ ID NO 11
<211> LENGTH: 192
<212> TYPE: PRT
<213> ORGANISM: Artificial sequence
<220> FEATURE:
<223> OTHER INFORMATION: Chimeric protein Chim3PdeltaN encoding the
      amino acid region 126-170 of F12-vif that has been inserted in a
      wild type-vif backbone.

<400> SEQUENCE: 11

Met Glu Asn Arg Trp Gln Val Met Ile Val Trp Gln Val Asp Arg Met
1               5                   10                  15

Arg Ile Asn Thr Trp Lys Arg Leu Val Lys His His Met Tyr Ile Ser
            20                  25                  30

Arg Lys Ala Lys Asp Trp Phe Tyr Arg His His Tyr Glu Ser Thr Asn
        35                  40                  45

Pro Lys Ile Ser Ser Glu Val His Ile Pro Leu Gly Asp Ala Lys Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110
```

-continued

```
Asp Cys Phe Ser Glu Ser Ala Ile Arg Asn Thr Ile Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
            180                 185                 190
```

<210> SEQ ID NO 12
<211> LENGTH: 598
<212> TYPE: DNA
<213> ORGANISM: Artificial sequence
<220> FEATURE:
<223> OTHER INFORMATION: Nucleotide encoding chimeric protein Chim1PdeltaN

<400> SEQUENCE: 12

```
atcgatggga ttatggaaaa cagatggcag gtgatgattg tgtggcaagt agacaggatg     60

aggattaaca catggaaaag attagtaaaa caccatatgt atatttcaag gaaagctaag    120

gactggtttt atagacatca ctatgaaagt actaatccaa aaataagttc agaagtacac    180

atcccactag ggatgctaa attagtaata acaacatatt ggggtctgca tacaggagaa    240

agagactggc atttgggtca gggagtctcc atagaatgga ggaaaaagag atatagcaca    300

caagtagacc ctgacctagc agaccaacta attcatctgc actattttga ttgtttttca    360

gaatctgcta taagaaatac catattagga aatgtagtta gacttagttg tgaatatcaa    420

gcaggacata acaagatagg atctctacaa tacttggcac tagcagcatt aataacacca    480

aaaaagataa agccaccttt gcctagtgtt acgaaactga cagaggacag atggaacaag    540

ccccagaaga ccaagggcca cagagggagc catacaatga atggacacta gcatcgat      598
```

<210> SEQ ID NO 13
<211> LENGTH: 599
<212> TYPE: DNA
<213> ORGANISM: Artificial sequence
<220> FEATURE:
<223> OTHER INFORMATION: Nucleotide encoding chimeric protein Chim2PdeltaN

<400> SEQUENCE: 13

```
tatcgatggg attatggaaa acagatggca ggtgatgatt gtgtggcaag tagacaggat     60

gaggattaac acatggaaaa gattagtaaa acaccatatg tatatttcaa ggaaagctaa    120

ggactggttt tatagacatc actatgaaag tactaatcca aaaataagtt cagaagtaca    180

catcccacta ggggatgcta aattagtaat aacaacatat tggggtctgc atacaggaga    240

aagagactgg catttgggtc agggagtctc catagaatgg aggaaaaaga gatatagcac    300

acaagtagac cctggcctag cagaccaact aattcatcgg tattattttg attgtttttc    360

agaatctgct ataagaaatg ccatactagg aaatgtagtt agacttagtt gtgaatatca    420

agcaggacat aacaagatag gatctctaca atacttggca ctagcagcat taataacacc    480

aaaaaagata aagccacctt tgcctagtgt tacgaaactg acagaggata gatggaacaa    540

gccccagaag accaagggcc acagaaggaa ccatacaatg aatggacact agatcgata     599
```

<210> SEQ ID NO 14

<211> LENGTH: 598
<212> TYPE: DNA
<213> ORGANISM: Artificial sequence
<220> FEATURE:
<223> OTHER INFORMATION: Nucleotide encoding chimeric protein
      Chim3deltaN

<400> SEQUENCE: 14

| | |
|---|---|
| atcgatggga ttatggaaaa cagatggcag gtgatgattg tgtggcaagt agacaggatg | 60 |
| aggattaaca catggaaaag attagtaaaa caccatatgt atatttcaag gaaagctaag | 120 |
| gactggtttt atagacatca ctatgaaagt actaatccaa aaataagttc agaagtacac | 180 |
| atcccactag gggatgctaa attagtaata acaacatatt ggggtctgca tacaggagaa | 240 |
| agagactggc atttgggtca gggagtctcc atagaatgga ggaaaaagag atatagcaca | 300 |
| caagtagacc ctggcctagc agaccaacta attcatcggt attattttga ttgtttttca | 360 |
| gaatctgcta taagaaatgc catactagga aatgtagtta gacttagttg tgaatatcaa | 420 |
| gcaggacata acaagatagg atctctacaa tacttggcac tagcagcatt aataacacca | 480 |
| aaaaagataa agccaccttt gcctagtgtt acgaaactga cagaggatag atggaacaag | 540 |
| ccccagaaga ccaagggcca cagaaggaac catacaatga atggacacta gatcgata | 598 |

<210> SEQ ID NO 15
<211> LENGTH: 598
<212> TYPE: DNA
<213> ORGANISM: Homo sapiens
<220> FEATURE:
<221> NAME/KEY: misc_feature
<223> OTHER INFORMATION: Human immunodeficiency virus

<400> SEQUENCE: 15

| | |
|---|---|
| atcgatggga ttatggaaaa cagatggcag gtgatgattg tgtggcaagt agacaggatg | 60 |
| aggattaaca catggaaaag attagtaaaa caccatatgt atatttcaag gaaagctaag | 120 |
| gactggtttt atagacatca ctatgaaagt actaatccaa aaataagttc agaagtacac | 180 |
| atcccactag gggatgctaa attagtaata acaacatatt ggggtctgca tacaggagaa | 240 |
| agagactggc atttgggtca gggagtctcc atagaatgga ggaaaaagag atatagcaca | 300 |
| caagtagacc ctgacctagc agaccaacta attcatctgc actattttga ttgtttttca | 360 |
| gaatctgcta taagaaatac catattagga cgtatagtta gtcctaggtg tgaatatcaa | 420 |
| gcaggacata acaaggtagg atctctacag tacttggcac tagcagcatt aataaaacca | 480 |
| aaacagataa agccaccttt gcctagtgtt aggaaactga cagaggacag atggaacaag | 540 |
| ccccagaaga ccaagggcca cagagggagc catacaatga atggacacta gcatcgat | 598 |

<210> SEQ ID NO 16
<211> LENGTH: 591
<212> TYPE: DNA
<213> ORGANISM: Homo sapiens
<220> FEATURE:
<221> NAME/KEY: misc_feature
<223> OTHER INFORMATION: Human immunodeficiency virus

<400> SEQUENCE: 16

| | |
|---|---|
| atcgatggga ttatggaaaa cagatggcag gtgatgattg tgtggcaagt agacaggatg | 60 |
| aggattagaa catggataag tttagtaaaa caccatatat atatttcaaa gaaagctaag | 120 |
| ggatggtttt ataaacatca ctatgaaagc actaatccaa gaataagttc agaagtacac | 180 |
| atcccactag gggatgctag attggtagta acaacatatt ggggtctgca tacaggagaa | 240 |

-continued

```
agagactgga atttaggcca gggagtctcc atagaatgga ggaaaaagag atatagcaca    300

caagtagacc ctggcctagc agaccaacta attcatcggt attattttga ttgtttttca    360

gaatctgcta taagaaatgc catactagga aatgtagtta gacttagttg tgaatatcaa    420

gcaggacata acaagatagg atctctacaa tacttggcac tagcagcatt aataacacca    480

aaaaagataa agccaccttt gcctagtgtt acgaaactga cagaggatag atggaacaag    540

ccccagaaga ccaagggcca cagaaggaac catacaatga atggacacta g             591


<210> SEQ ID NO 17
<211> LENGTH: 30
<212> TYPE: DNA
<213> ORGANISM: Artificial sequence
<220> FEATURE:
<223> OTHER INFORMATION: Synthetic primer

<400> SEQUENCE: 17

gcaaagaatc gatgggatta tggaaaacag                                      30


<210> SEQ ID NO 18
<211> LENGTH: 32
<212> TYPE: DNA
<213> ORGANISM: Artificial sequence
<220> FEATURE:
<223> OTHER INFORMATION: Synthetic primer

<400> SEQUENCE: 18

ctcctctaat cgatgctagt gtccattcat tg                                   32


<210> SEQ ID NO 19
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val

<400> SEQUENCE: 19

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30
```

```
Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
            180                 185                 190


<210> SEQ ID NO 20
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn

<400> SEQUENCE: 20

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
```

180 185 190

<210> SEQ ID NO 21
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly

<400> SEQUENCE: 21

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Ser His Thr Met Asn Gly His
            180                 185                 190
```

<210> SEQ ID NO 22
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn

<400> SEQUENCE: 22

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Ser His Thr Met Asn Gly His
            180                 185                 190
```

<210> SEQ ID NO 23
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:

<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly
<220> FEATURE:
<221> NAME/KEY: Mutagen
<222> LOCATION: (186)..(186)
<223> OTHER INFORMATION: May be any amino acid except Ser

<400> SEQUENCE: 23

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Xaa His Thr Met Asn Gly His
            180                 185                 190
```

<210> SEQ ID NO 24
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn

<400> SEQUENCE: 24

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60
```

```
Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190


<210> SEQ ID NO 25
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn
<220> FEATURE:
<221> NAME/KEY: Mutagen
<222> LOCATION: (109)..(109)
<223> OTHER INFORMATION: May be any amino acid except Leu
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly
<220> FEATURE:
<221> NAME/KEY: Mutagen
<222> LOCATION: (186)..(186)
<223> OTHER INFORMATION: May be any amino acid except Ser

<400> SEQUENCE: 25

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
```

-continued

```
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Xaa His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Xaa His Thr Met Asn Gly His
            180                 185                 190


<210> SEQ ID NO 26
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn

<400> SEQUENCE: 26

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Arg His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175
```

```
Pro Gln Lys Thr Lys Gly His Arg Arg Asn His Thr Met Asn Gly His
            180                 185                 190


<210> SEQ ID NO 27
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn
<220> FEATURE:
<221> NAME/KEY: Mutagen
<222> LOCATION: (80)..(80)
<223> OTHER INFORMATION: May be any amino acid except His
<220> FEATURE:
<221> NAME/KEY: Mutagen
<222> LOCATION: (109)..(109)
<223> OTHER INFORMATION: May be any amino acid except Leu
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly
<220> FEATURE:
<221> NAME/KEY: Mutagen
<222> LOCATION: (186)..(186)
<223> OTHER INFORMATION: May be any amino acid except Ser

<400> SEQUENCE: 27

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp Xaa
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Xaa His Tyr Phe
            100                 105                 110

Asp Cys Phe Ser Glu Ser Ala Ile Arg Lys Ala Leu Leu Gly Xaa Xaa
```

```
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Xaa His Thr Met Asn Gly His
            180                 185                 190


<210> SEQ ID NO 28
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn

<400> SEQUENCE: 28

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Arg His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190


<210> SEQ ID NO 29
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn
<220> FEATURE:
<221> NAME/KEY: Mutagen
<222> LOCATION: (66)..(66)
<223> OTHER INFORMATION: May be any amino acid except Ile
```

<220> FEATURE:
<221> NAME/KEY: Mutagen
<222> LOCATION: (80)..(80)
<223> OTHER INFORMATION: May be any amino acid except His
<220> FEATURE:
<221> NAME/KEY: Mutagen
<222> LOCATION: (109)..(109)
<223> OTHER INFORMATION: May be any amino acid except Leu
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly
<220> FEATURE:
<221> NAME/KEY: Mutagen
<222> LOCATION: (186)..(186)
<223> OTHER INFORMATION: May be any amino acid except Ser

<400> SEQUENCE: 29

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Xaa Thr Thr Tyr Trp Gly Leu His Thr Gly Glu Arg Asp Trp Xaa
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Xaa His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Xaa His Thr Met Asn Gly His
            180                 185                 190
```

<210> SEQ ID NO 30
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be His or Asn

<400> SEQUENCE: 30

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Arg His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190
```

<210> SEQ ID NO 31
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (48)..(48)
<223> OTHER INFORMATION: May be any amino acid except His
<220> FEATURE:
<221> NAME/KEY: Mutagen
<222> LOCATION: (66)..(66)
<223> OTHER INFORMATION: May be any amino acid except Ile
<220> FEATURE:
<221> NAME/KEY: Mutagen
<222> LOCATION: (80)..(80)
<223> OTHER INFORMATION: May be any amino acid except His
<220> FEATURE:
<221> NAME/KEY: Mutagen
<222> LOCATION: (109)..(109)
<223> OTHER INFORMATION: May be any amino acid except Leu
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly
<220> FEATURE:
<221> NAME/KEY: Mutagen
<222> LOCATION: (186)..(186)
<223> OTHER INFORMATION: May be any amino acid except Ser

<400> SEQUENCE: 31

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro Xaa
        35                  40                  45

Pro Arg Ile Ser Ser Glu Val His Ile Pro Leu Gly Asp Ala Arg Leu
    50                  55                  60

Val Xaa Thr Thr Tyr Trp Gly Leu His Thr Gly Glu Arg Asp Trp Xaa
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Xaa His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Xaa His Thr Met Asn Gly His
            180                 185                 190
```

<210> SEQ ID NO 32
<211> LENGTH: 192
<212> TYPE: PRT
<213> ORGANISM: Artificial sequence
<220> FEATURE:
<223> OTHER INFORMATION: Mutant HIV-VIF sequence

<400> SEQUENCE: 32

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
```

```
            20                  25                  30

Gly Lys Ala Arg Gly Trp Phe Tyr Arg His His Tyr Glu Ser Pro Asn
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Arg His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190


<210> SEQ ID NO 33
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (41)..(41)
<223> OTHER INFORMATION: May be any amino acid except Arg
<220> FEATURE:
<221> NAME/KEY: Mutagen
<222> LOCATION: (48)..(48)
<223> OTHER INFORMATION: May be any amino acid except His
<220> FEATURE:
<221> NAME/KEY: Mutagen
<222> LOCATION: (66)..(66)
<223> OTHER INFORMATION: May be any amino acid except Ile
<220> FEATURE:
<221> NAME/KEY: Mutagen
<222> LOCATION: (80)..(80)
<223> OTHER INFORMATION: May be any amino acid except His
<220> FEATURE:
<221> NAME/KEY: Mutagen
<222> LOCATION: (109)..(109)
<223> OTHER INFORMATION: May be any amino acid except Leu
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
```

<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly
<220> FEATURE:
<221> NAME/KEY: Mutagen
<222> LOCATION: (186)..(186)
<223> OTHER INFORMATION: May be any amino acid except Ser

<400> SEQUENCE: 33

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Xaa His His Tyr Glu Ser Pro Xaa
        35                  40                  45

Pro Arg Ile Ser Ser Glu Val His Ile Pro Leu Gly Asp Ala Arg Leu
    50                  55                  60

Val Xaa Thr Thr Tyr Trp Gly Leu His Thr Gly Glu Arg Asp Trp Xaa
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Xaa His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Xaa His Thr Met Asn Gly His
            180                 185                 190
```

<210> SEQ ID NO 34
<211> LENGTH: 192
<212> TYPE: PRT
<213> ORGANISM: Artificial sequence
<220> FEATURE:
<223> OTHER INFORMATION: Mutant HIV-VIF sequence

<400> SEQUENCE: 34

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Lys His His Tyr Glu Ser Pro Asn
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95
```

-continued

```
Gln Val Asp Pro Glu Leu Ala Asp Gln Leu Ile His Arg His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190


<210> SEQ ID NO 35
<211> LENGTH: 192
<212> TYPE: PRT
<213> ORGANISM: Artificial sequence
<220> FEATURE:
<223> OTHER INFORMATION: Mutant HIV-VIF sequence
<220> FEATURE:
<221> NAME/KEY: Mutagen
<222> LOCATION: (29)..(29)
<223> OTHER INFORMATION: May be any amino acid except Met
<220> FEATURE:
<221> NAME/KEY: Mutagen
<222> LOCATION: (41)..(41)
<223> OTHER INFORMATION: May be any amino acid except Arg
<220> FEATURE:
<221> NAME/KEY: Mutagen
<222> LOCATION: (48)..(48)
<223> OTHER INFORMATION: May be any amino acid except His
<220> FEATURE:
<221> NAME/KEY: Mutagen
<222> LOCATION: (66)..(66)
<223> OTHER INFORMATION: May be any amino acid except Ile
<220> FEATURE:
<221> NAME/KEY: Mutagen
<222> LOCATION: (80)..(80)
<223> OTHER INFORMATION: May be any amino acid except His
<220> FEATURE:
<221> NAME/KEY: Mutagen
<222> LOCATION: (109)..(109)
<223> OTHER INFORMATION: May be any amino acid except Leu
<220> FEATURE:
<221> NAME/KEY: Mutagen
<222> LOCATION: (127)..(127)
<223> OTHER INFORMATION: May be any amino acid except His
<220> FEATURE:
<221> NAME/KEY: Mutagen
<222> LOCATION: (128)..(128)
<223> OTHER INFORMATION: May be any amino acid except Ile
<220> FEATURE:
<221> NAME/KEY: Mutagen
<222> LOCATION: (130)..(130)
<223> OTHER INFORMATION: May be any amino acid except Ser
<220> FEATURE:
<221> NAME/KEY: Mutagen
<222> LOCATION: (131)..(131)
<223> OTHER INFORMATION: May be any amino acid except Pro
<220> FEATURE:
<221> NAME/KEY: Mutagen
<222> LOCATION: (132)..(132)
<223> OTHER INFORMATION: May be any amino acid except Arg
<220> FEATURE:
<221> NAME/KEY: Mutagen
<222> LOCATION: (142)..(142)
<223> OTHER INFORMATION: May be any amino acid except Val
<220> FEATURE:
<221> NAME/KEY: Mutagen
<222> LOCATION: (185)..(185)
<223> OTHER INFORMATION: May be any amino acid except Gly
<220> FEATURE:
<221> NAME/KEY: Mutagen
```

<222> LOCATION: (186)..(186)
<223> OTHER INFORMATION: May be any amino acid except Ser

<400> SEQUENCE: 35

```
Met Glu Asn Arg Trp Gln Val Met Ile Val Trp Gln Val Asp Arg Met
1               5                   10                  15

Arg Ile Arg Thr Trp Lys Ser Leu Val Lys His His Xaa Tyr Val Ser
            20                  25                  30

Gly Lys Ala Arg Gly Trp Phe Tyr Xaa His His Tyr Glu Ser Pro Xaa
        35                  40                  45

Pro Arg Ile Ser Ser Glu Val His Ile Pro Leu Gly Asp Ala Arg Leu
    50                  55                  60

Val Xaa Thr Thr Tyr Trp Gly Leu His Thr Gly Glu Arg Asp Trp Xaa
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Xaa His Tyr Phe
            100                 105                 110

Asp Cys Phe Ser Glu Ser Ala Ile Arg Lys Ala Leu Leu Gly Xaa Xaa
        115                 120                 125

Val Xaa Xaa Xaa Cys Glu Tyr Gln Ala Gly His Asn Lys Xaa Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Xaa Xaa His Thr Met Asn Gly His
            180                 185                 190
```

<210> SEQ ID NO 36
<211> LENGTH: 192
<212> TYPE: PRT
<213> ORGANISM: Artificial sequence
<220> FEATURE:
<223> OTHER INFORMATION: Mutant HIV-VIF sequence

<400> SEQUENCE: 36

```
Met Glu Asn Arg Trp Gln Val Met Ile Val Trp Gln Val Asp Arg Met
1               5                   10                  15

Arg Ile Arg Thr Trp Lys Ser Leu Val Lys His His Ile Tyr Val Ser
            20                  25                  30

Gly Lys Ala Arg Gly Trp Phe Tyr Lys His His Tyr Glu Ser Pro Asn
        35                  40                  45

Pro Arg Ile Ser Ser Glu Val His Ile Pro Leu Gly Asp Ala Arg Leu
    50                  55                  60

Val Val Thr Thr Tyr Trp Gly Leu His Thr Gly Glu Arg Asp Trp Asn
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Arg His Tyr Phe
            100                 105                 110

Asp Cys Phe Ser Glu Ser Ala Ile Arg Lys Ala Leu Leu Gly Asn Val
        115                 120                 125

Val Arg Leu Ser Cys Glu Tyr Gln Ala Gly His Asn Lys Ile Gly Ser
    130                 135                 140

Leu Gln Tyr Leu Ala Leu Ala Ala Leu Ile Thr Pro Lys Lys Ile Lys
```

-continued

```
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Arg Asn His Thr Met Asn Gly His
            180                 185                 190


<210> SEQ ID NO 37
<211> LENGTH: 45
<212> TYPE: PRT
<213> ORGANISM: Artificial sequence
<220> FEATURE:
<223> OTHER INFORMATION: Region of F12-VIF (Chim3)

<400> SEQUENCE: 37

Gly Asn Val Val Arg Leu Ser Cys Glu Tyr Gln Ala Gly His Asn Lys
1               5                   10                  15

Ile Gly Ser Leu Gln Tyr Leu Ala Leu Ala Ala Leu Ile Thr Pro Lys
            20                  25                  30

Lys Ile Lys Pro Pro Leu Pro Ser Val Thr Lys Leu Thr
        35                  40                  45
```